(12) United States Patent
Chin et al.

(10) Patent No.: US 7,947,059 B2
(45) Date of Patent: May 24, 2011

(54) MULTILAYER MEDICAL DEVICE

(75) Inventors: Albert C. C. Chin, Newton, MA (US);
John Jianhua Chen, Plymouth, MN (US); Yiqun Wang, Maple Grove, MN (US); David W. Lodin, Zimmerman, MN (US); Lixiao Wang, Long Lake, MN (US); Ronald A. Sahatjian, Lexington, MA (US); Ismail Guler, Minneapolis, MN (US); Robert Burgmeier, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 255 days.

(21) Appl. No.: 09/798,749

(22) Filed: Mar. 2, 2001

(65) Prior Publication Data
US 2002/0165523 A1 Nov. 7, 2002

Related U.S. Application Data

(63) Continuation-in-part of application No. 09/517,870, filed on Mar. 2, 2000, now abandoned.

(51) Int. Cl.
*A61M 25/10* (2006.01)
(52) U.S. Cl. .................... 606/192; 604/103.06
(58) Field of Classification Search .......... 606/191, 606/192, 194; 604/96.01, 101.02, 103.06; 264/239, 36.15; 428/34.1
See application file for complete search history.

(56) References Cited

U.S. PATENT DOCUMENTS

| | | |
|---|---|---|
| 3,561,493 A | 2/1971 | Maillard et al. |
| 3,618,614 A | 11/1971 | Flynn |
| 3,924,634 A | 12/1975 | Taylor et al. |
| 3,993,812 A | 11/1976 | Debbas et al. |
| 4,044,180 A | 8/1977 | Baker |
| 4,047,868 A | 9/1977 | Kudo et al. |
| 4,079,850 A | 3/1978 | Suzuki et al. |
| 4,174,783 A | 11/1979 | Abe et al. |
| 4,182,457 A | 1/1980 | Yamada et al. |
| 4,211,741 A | 7/1980 | Ostoich |
| 4,244,914 A | 1/1981 | Ranalli et al. |
| 4,282,876 A | 8/1981 | Flynn |
| 4,296,156 A | 10/1981 | Lustig et al. |
| 4,327,736 A | 5/1982 | Inoue |
| 4,335,723 A | 6/1982 | Patel |
| 4,409,364 A | 10/1983 | Schmukler et al. |
| 4,424,242 A | 1/1984 | Barbee |
| 4,472,129 A | 9/1984 | Siard |
| 4,484,971 A | 11/1984 | Wang |

(Continued)

FOREIGN PATENT DOCUMENTS
DE 28 48 854 5/1979
(Continued)

OTHER PUBLICATIONS

Rigid Plastics Are Getting a Foot in the Kitchen Door, Chemicalweek, McGraw-Hill Publication, Oct. 12, 1983.
Developments in Cast and Blown Film, Plastic Technology, Aug. 1987, vol. 33 #9, p. 39 & 41.

(Continued)

*Primary Examiner* — (Jackie) Tan-Uyen T Ho
*Assistant Examiner* — Ryan J Severson
(74) *Attorney, Agent, or Firm* — Vidas, Arrett & Steinkraus

(57) ABSTRACT

A medical device such as a tube or a balloon including wall structure with multiple layers. The wall structure can distribute stress, resulting in reduced defect propagation and failure.

13 Claims, 19 Drawing Sheets

U.S. PATENT DOCUMENTS

| | | |
|---|---|---|
| 4,490,421 A | 12/1984 | Levy |
| 4,551,292 A | 11/1985 | Fletcher et al. |
| 4,578,024 A | 3/1986 | Sicka et al. |
| 4,596,563 A | 6/1986 | Pande |
| 4,627,844 A | 12/1986 | Schmitt |
| 4,634,615 A | 1/1987 | Versteegh et al. |
| 4,636,346 A | 1/1987 | Gold et al. |
| 4,636,442 A | 1/1987 | Beavers et al. |
| 4,640,852 A | 2/1987 | Ossian |
| 4,648,871 A | 3/1987 | Jacob |
| 4,656,070 A | 4/1987 | Nyberg et al. |
| 4,677,017 A | 6/1987 | DeAntonis et al. |
| 4,686,124 A | 8/1987 | Onohara et al. |
| 4,753,765 A | 6/1988 | Pande |
| 4,778,697 A | 10/1988 | Genske et al. |
| 4,790,831 A | 12/1988 | Skribiski |
| 4,814,231 A | 3/1989 | Onohara et al. |
| 4,816,339 A | 3/1989 | Tu et al. |
| 4,818,592 A | 4/1989 | Ossian |
| 4,824,618 A | 4/1989 | Strum et al. |
| 4,834,721 A | 5/1989 | Onohara et al. |
| 4,840,623 A | 6/1989 | Quackenbush |
| RE32,983 E | 7/1989 | Levy |
| 4,863,426 A | 9/1989 | Ferragamo et al. |
| 4,880,682 A | 11/1989 | Hazelton et al. |
| 4,906,244 A | 3/1990 | Pinchuk et al. |
| 4,917,088 A * | 4/1990 | Crittenden ............... 606/194 |
| 4,932,956 A | 6/1990 | Reddy et al. |
| 4,952,357 A | 8/1990 | Euteneuer |
| 4,963,306 A | 10/1990 | Weldon |
| 4,994,047 A | 2/1991 | Walker et al. |
| 5,041,089 A | 8/1991 | Mueller et al. |
| 5,059,269 A | 10/1991 | Hu et al. |
| 5,071,686 A | 12/1991 | Genske et al. |
| 5,076,776 A | 12/1991 | Yamada et al. |
| 5,093,164 A | 3/1992 | Bauer et al. |
| 5,094,799 A | 3/1992 | Takashige et al. |
| 5,100,721 A | 3/1992 | Akao |
| 5,108,415 A | 4/1992 | Pinchuk et al. |
| 5,125,913 A | 6/1992 | Quackenbush |
| 5,156,857 A | 10/1992 | Wang et al. |
| 5,171,221 A | 12/1992 | Samson |
| 5,195,969 A | 3/1993 | Wang et al. |
| 5,201,706 A | 4/1993 | Noguchi et al. |
| 5,205,822 A * | 4/1993 | Johnson et al. ............. 606/192 |
| 5,223,205 A | 6/1993 | Jackowski et al. |
| 5,254,090 A | 10/1993 | Lombardi et al. |
| 5,270,086 A * | 12/1993 | Hamlin ................. 428/35.2 |
| 5,277,199 A | 1/1994 | DuBois et al. |
| 5,290,306 A | 3/1994 | Trotta et al. |
| 5,304,197 A | 4/1994 | Pinchuk et al. |
| 5,306,246 A | 4/1994 | Sahatjian et al. |
| 5,318,041 A | 6/1994 | DuBois et al. |
| 5,330,428 A | 7/1994 | Wang et al. |
| 5,330,429 A | 7/1994 | Noguchi et al. |
| 5,344,401 A | 9/1994 | Radisch et al. |
| 5,356,709 A | 10/1994 | Woo et al. |
| 5,358,486 A | 10/1994 | Saab |
| 5,366,442 A | 11/1994 | Wang et al. |
| 5,417,671 A | 5/1995 | Jackson |
| 5,427,842 A | 6/1995 | Bland et al. |
| 5,439,454 A | 8/1995 | Lo et al. |
| 5,478,320 A | 12/1995 | Trotta |
| 5,509,899 A | 4/1996 | Fan et al. |
| 5,512,051 A * | 4/1996 | Wang et al. |
| 5,556,383 A * | 9/1996 | Wang et al. ............. 604/103.11 |
| 5,562,127 A | 10/1996 | Fanselow et al. |
| 5,565,530 A * | 10/1996 | Hattori et al. .................. 525/419 |
| 5,587,125 A | 12/1996 | Roychowdhury |
| 5,613,979 A | 3/1997 | Trotta et al. |
| 5,620,649 A | 4/1997 | Trotta |
| 5,669,920 A | 9/1997 | Conley et al. |
| 5,755,690 A | 5/1998 | Saab |
| 5,769,817 A | 6/1998 | Burgmeier |
| 5,792,105 A | 8/1998 | Lin et al. |
| 5,797,877 A | 8/1998 | Hamilton et al. |
| 5,820,594 A | 10/1998 | Fontirroche et al. |
| 5,824,173 A | 10/1998 | Fontirroche et al. |
| 5,833,657 A | 11/1998 | Reinhardt et al. |
| 5,843,032 A | 12/1998 | Kastenhofer |
| 5,851,464 A | 12/1998 | Davila et al. |
| 5,871,468 A | 2/1999 | Kramer et al. |
| 5,879,369 A * | 3/1999 | Ishida ............................ 606/194 |
| 5,908,406 A | 6/1999 | Ostapchenko et al. |
| 5,961,765 A | 10/1999 | Kastenhofer |
| 6,004,289 A | 12/1999 | Saab |
| 6,010,521 A | 1/2000 | Lee et al. |
| 6,027,477 A | 2/2000 | Kastenhofer |
| 6,059,751 A | 5/2000 | Ostapchenko et al. |
| 6,086,556 A | 7/2000 | Hamilton et al. |
| 6,124,007 A | 9/2000 | Wang et al. |
| 6,132,824 A | 10/2000 | Hamlin |
| 6,136,258 A | 10/2000 | Wang et al. |
| 6,136,394 A | 10/2000 | Karsten |
| 6,165,166 A | 12/2000 | Samuelson et al. |
| 6,242,063 B1 | 6/2001 | Ferrera et al. |
| 6,319,228 B1 | 11/2001 | Kastenhofer |
| 6,335,101 B1 | 1/2002 | Haeger et al. |
| 6,343,919 B1 | 2/2002 | Rodriguez et al. |
| 6,444,324 B1 | 9/2002 | Yang et al. |
| 6,447,835 B1 | 9/2002 | Wang et al. |
| 6,464,683 B1 | 10/2002 | Samuelson et al. |
| 6,471,673 B1 | 10/2002 | Kastenhofer |
| 6,482,348 B1 | 11/2002 | Wang et al. |
| 6,488,655 B1 | 12/2002 | Wantink et al. |
| 6,951,675 B2 | 10/2005 | Chin et al. |
| 2001/0043998 A1 | 11/2001 | Chen et al. |
| 2002/0165523 A1 | 11/2002 | Chen et al. |
| 2004/0078052 A1 | 4/2004 | St. Pierre et al. |
| 2005/0266109 A1 | 12/2005 | Chin et al. |

FOREIGN PATENT DOCUMENTS

| | | |
|---|---|---|
| DE | 3638828 | 5/1988 |
| EP | 0 095 521 A1 | 12/1983 |
| EP | 0 101 213 | 2/1984 |
| EP | 0 101 216 | 2/1984 |
| EP | 0 201 331 | 11/1986 |
| EP | 0 174 206 | 12/1986 |
| EP | 0 276 908 | 8/1988 |
| EP | 0 292 587 | 11/1988 |
| EP | 0 420 488 | 4/1991 |
| EP | 0 428 479 | 5/1991 |
| EP | 0 457 456 | 11/1991 |
| EP | 0 461 474 | 12/1991 |
| EP | 0803264 A1 | 10/1997 |
| FR | 998.035 | 1/1952 |
| FR | 2 328 482 | 5/1977 |
| GB | 1 556 242 | 10/1976 |
| GB | 1 533 204 | 9/1977 |
| GB | 1 600 963 | 5/1978 |
| GB | 2 077 111 | 6/1980 |
| GB | 2 078 114 | 12/1981 |
| GB | 2 140 437 | 11/1984 |
| GB | 2 163 386 | 2/1986 |
| JP | 51-084877 | 7/1976 |
| JP | 7 8045-353 | 12/1978 |
| JP | 53-45353 | 12/1978 |
| JP | 58-038778 | 3/1983 |
| JP | 58038778 | 3/1983 |
| JP | 2-43036 | 2/1990 |
| JP | 3-277374 | 12/1991 |
| JP | 4-34590 | 2/1992 |
| JP | 4-259537 | 9/1992 |
| SU | 1477423 | 5/1989 |
| WO | WO 84/01327 | 4/1984 |
| WO | WO 91/04068 | 4/1991 |
| WO | WO 92/11893 | 7/1992 |
| WO | WO92/19316 | 11/1992 |
| WO | WO96/04951 | 2/1996 |
| WO | WO97/32624 | 9/1997 |
| WO | WO 99/12586 | 3/1999 |
| WO | WO 01/32398 | 5/2001 |

OTHER PUBLICATIONS

William J. Broad, Plastics Revolution: A Rush of New Uses, The New York Times, Science Times, Tuesday, Nov. 1, 1983.

The Gamma bottle, Food & Drug Packaging, Oct. 1988, p. 34-36.

Squeezable bottle ends long wait for ketchup, Food & Drug Packaging, Oct. 1983, vol. 47, #10.

Extruded tubing is called on to perform more complex and critical surgical jobs, Modern Plastics International, Apr. 1990, p. 40-41.

Christopher Irwin, Blow Molding, Modern Plastics Encyclopedia, 1988, p. 203-210.

International Search Report PCT US 03/20861.

* cited by examiner

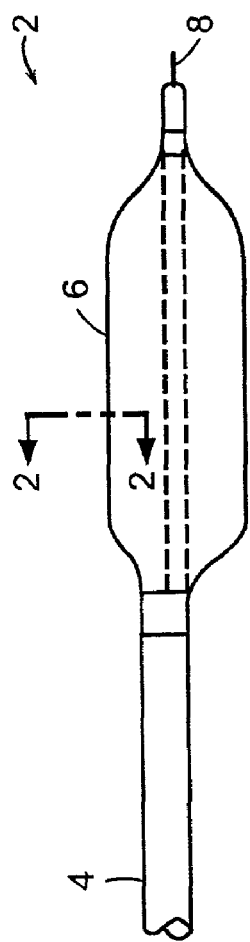
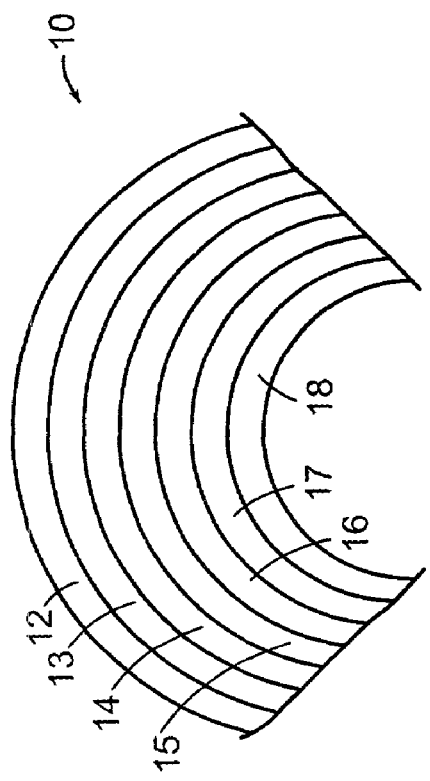
FIG. 1
FIG. 2

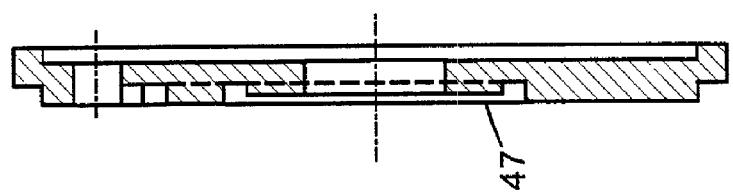
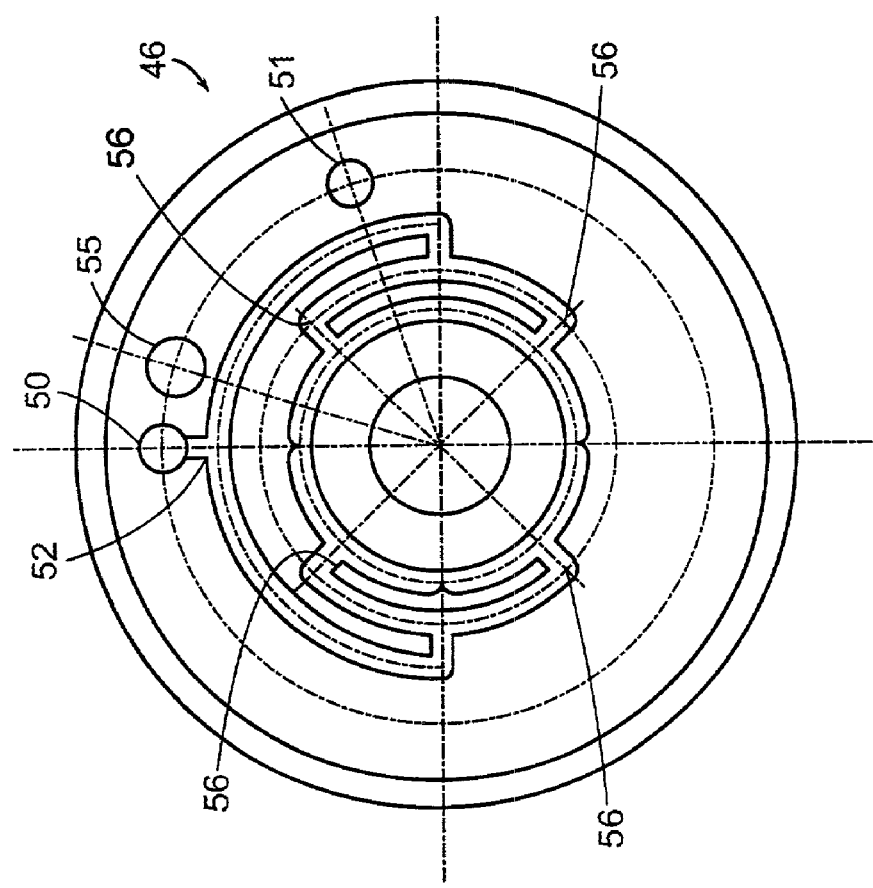

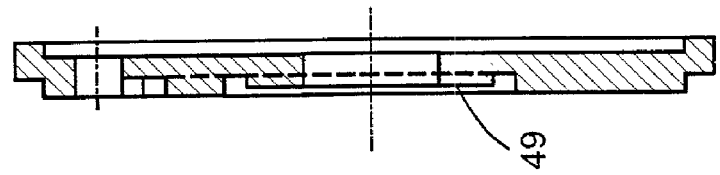
FIG. 3B1
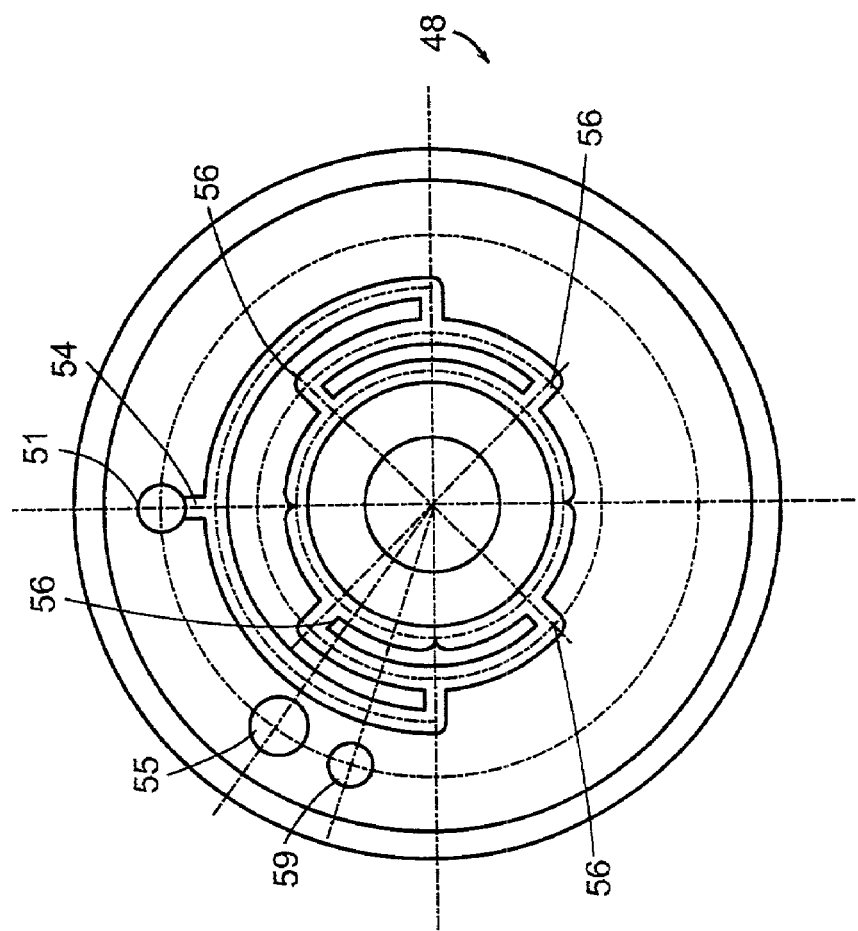
FIG. 3B

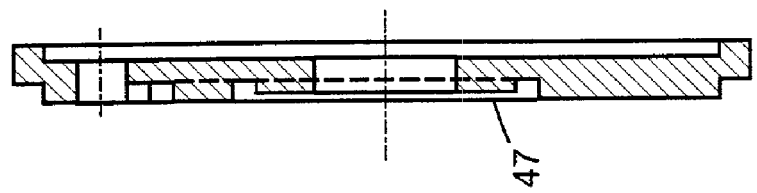
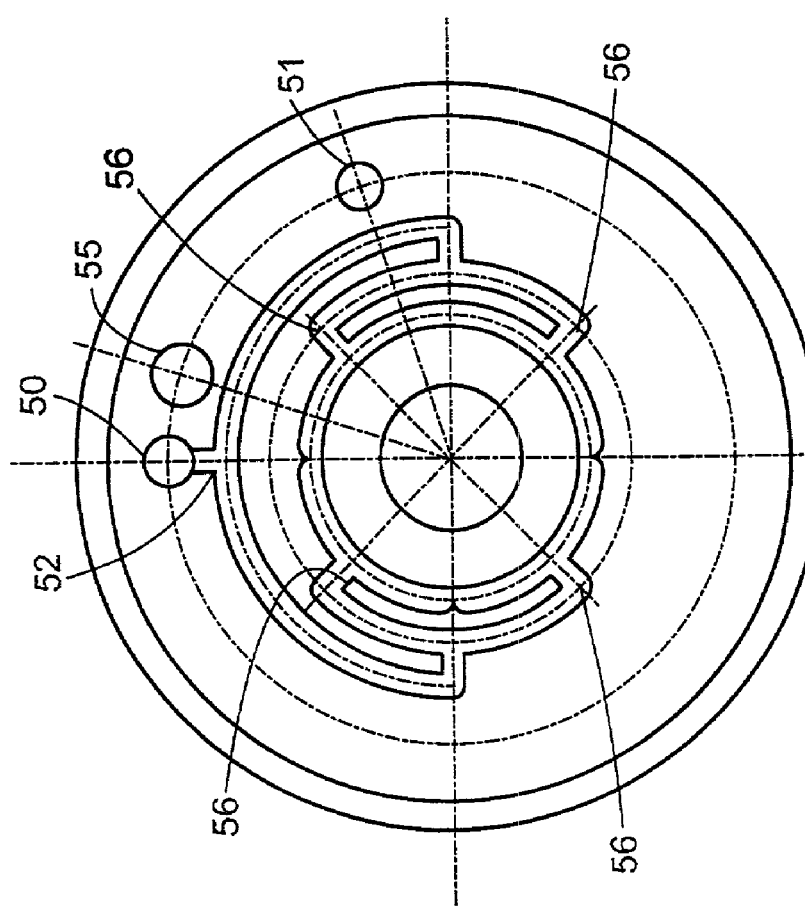

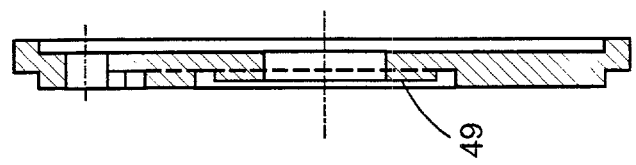
FIG. 3D1
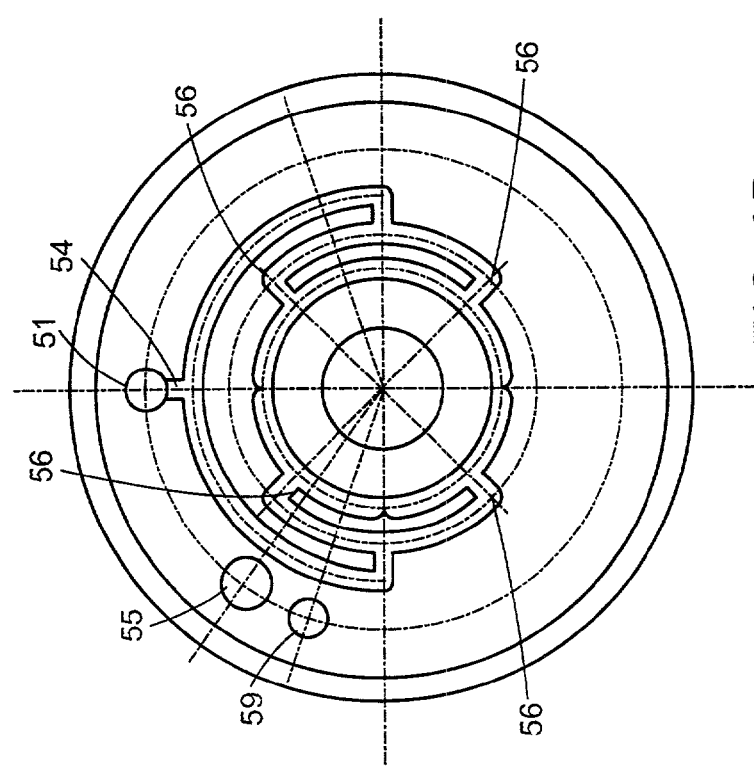
FIG. 3D

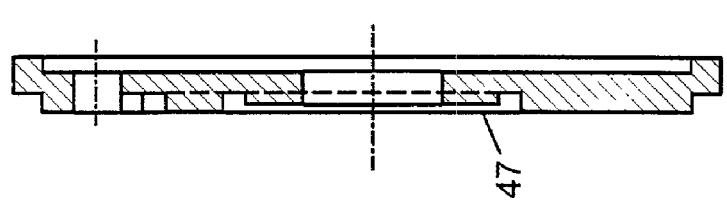
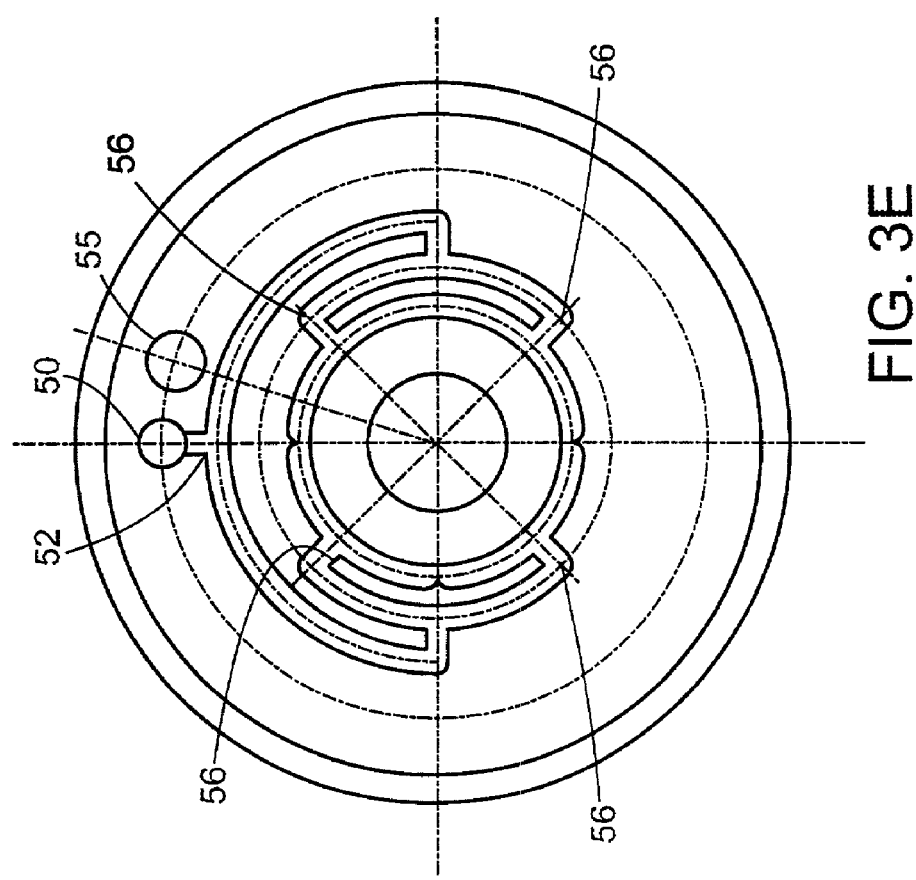

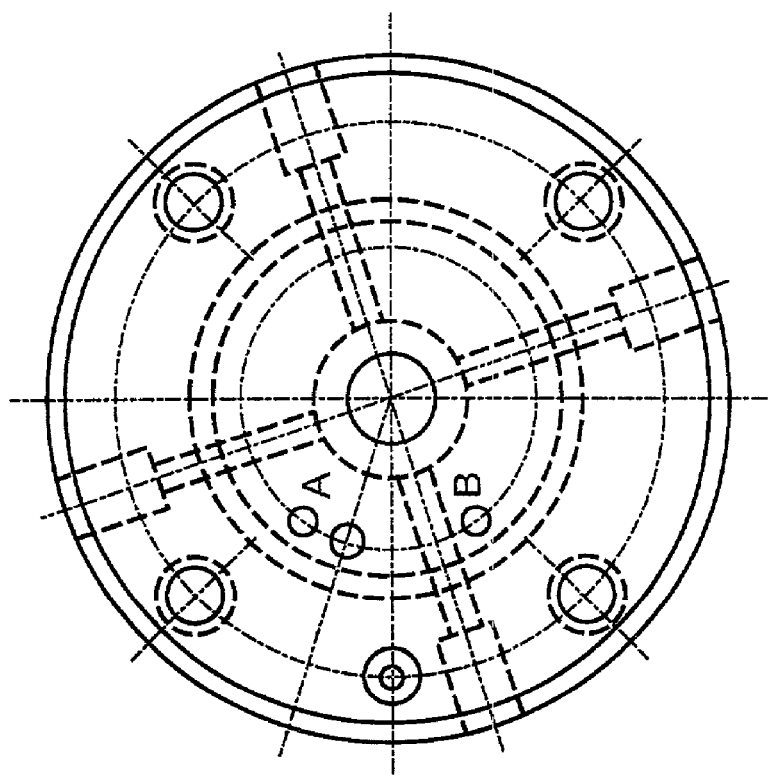
FIG. 3F1
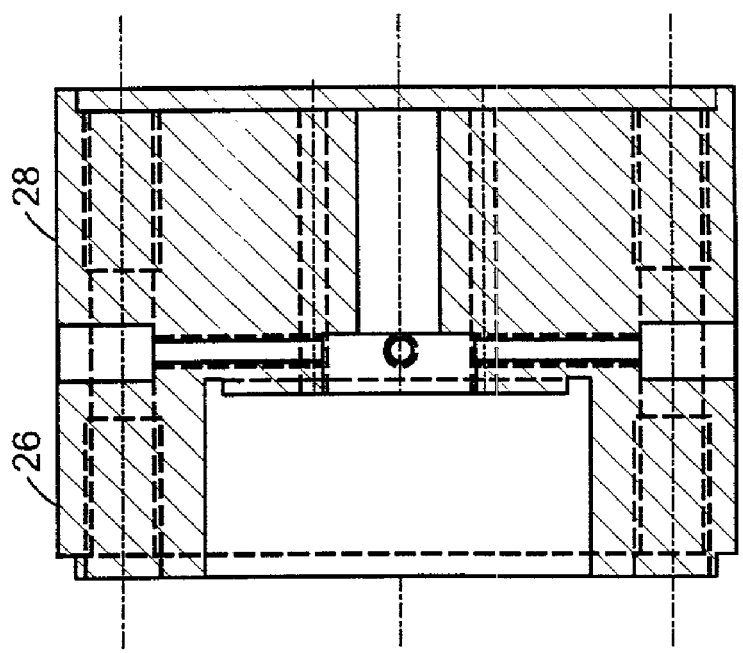
FIG. 3F

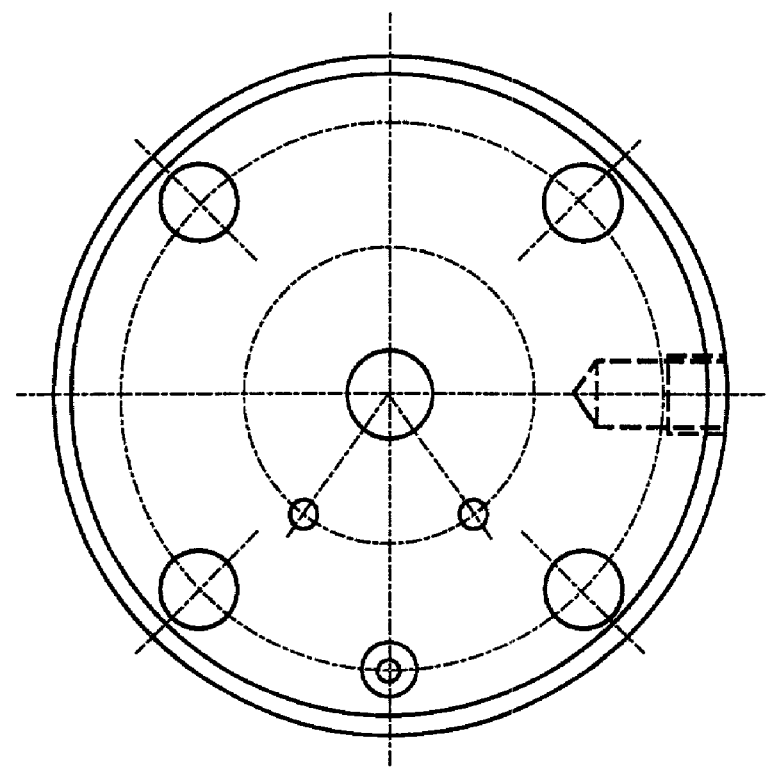
FIG. 3G1
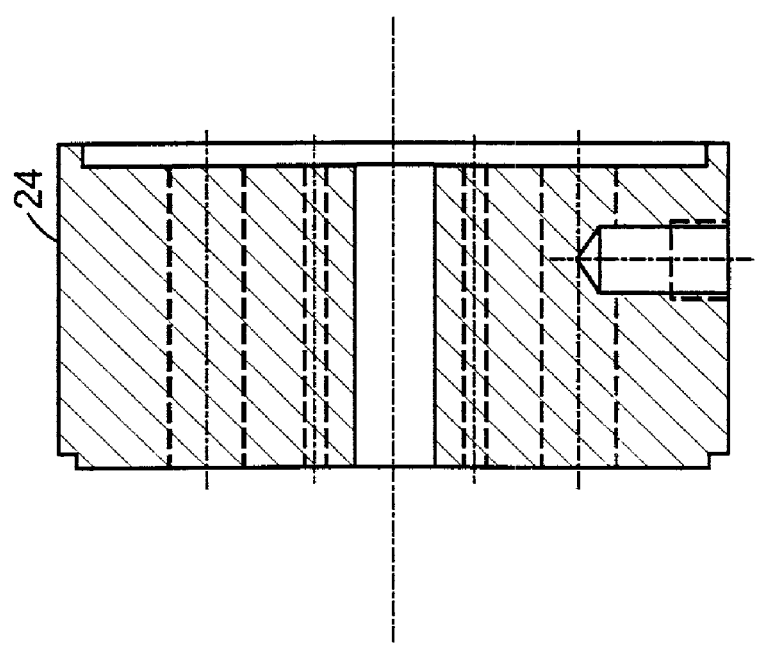
FIG. 3G

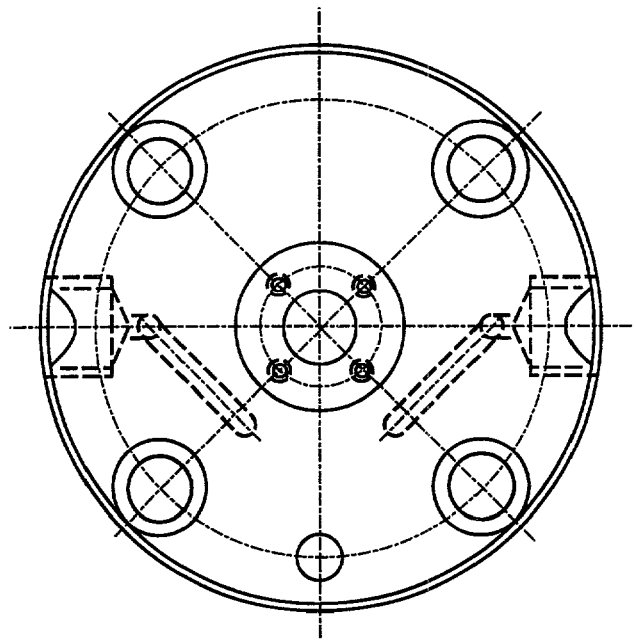
FIG. 3H2
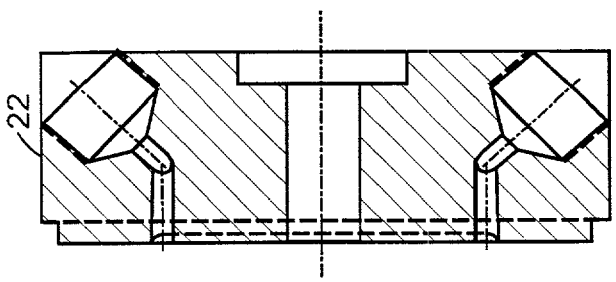
FIG. 3H1
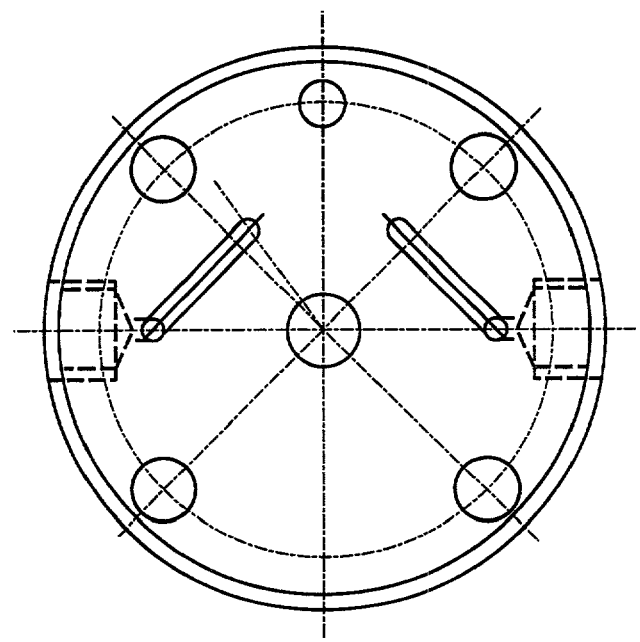
FIG. 3H

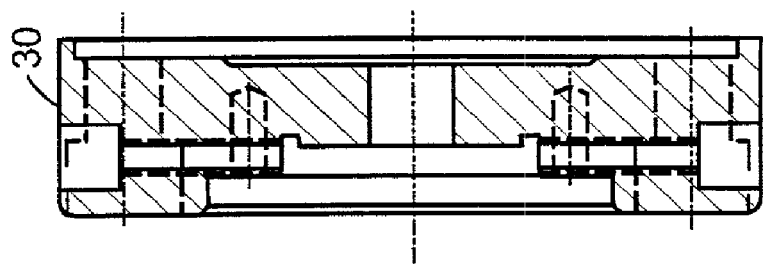
FIG. 3J1
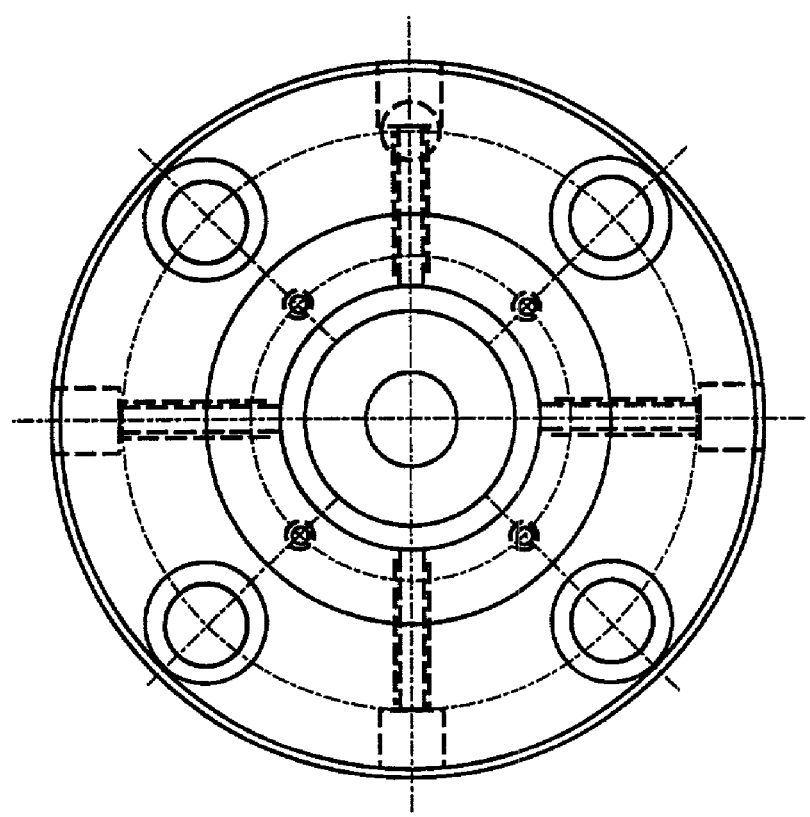
FIG. 3J

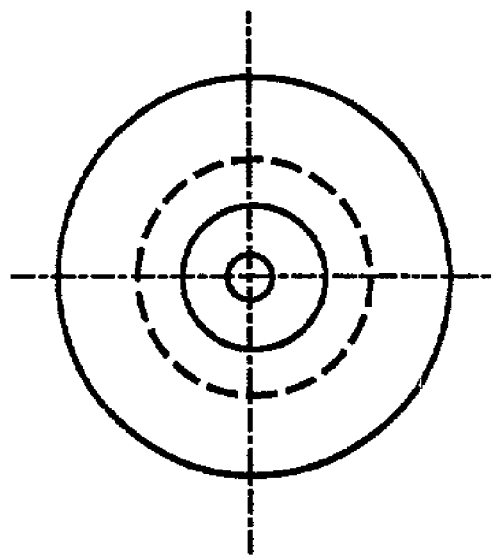
FIG. 3K1
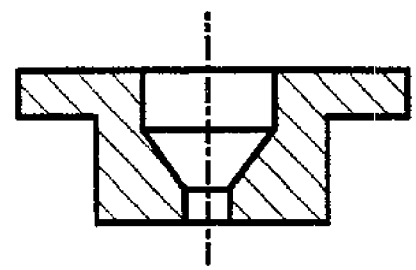
FIG. 3K

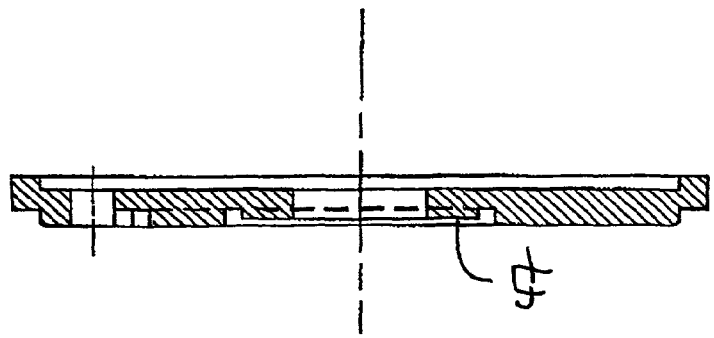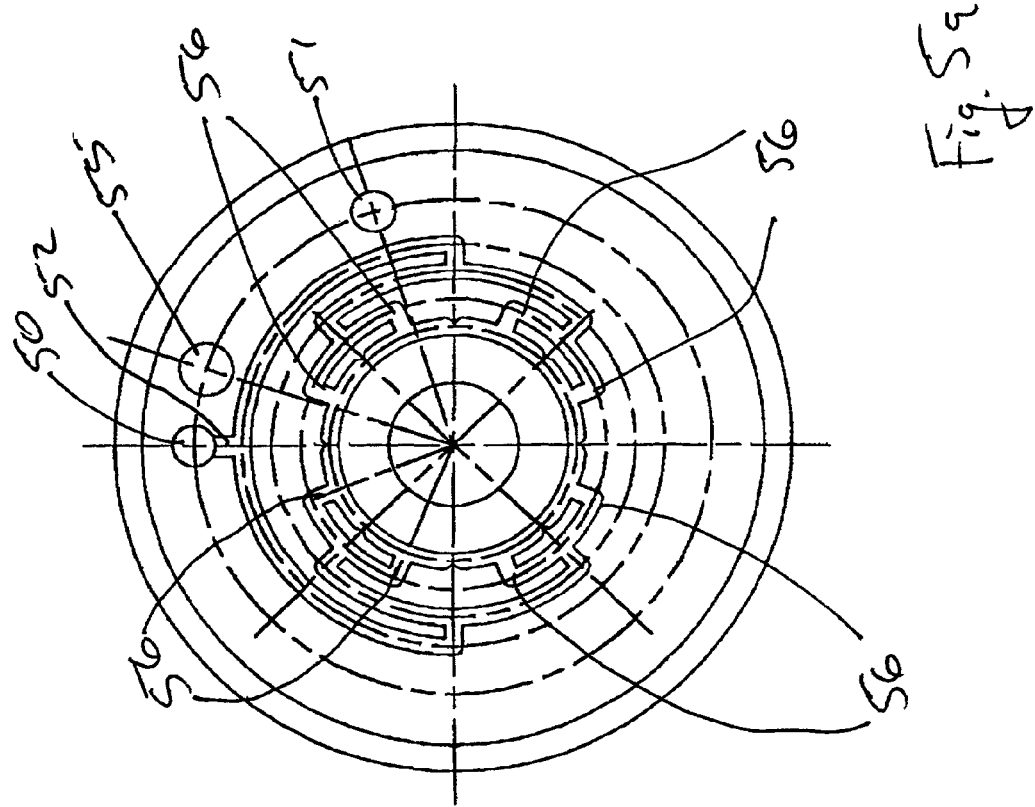
Fig. 5a

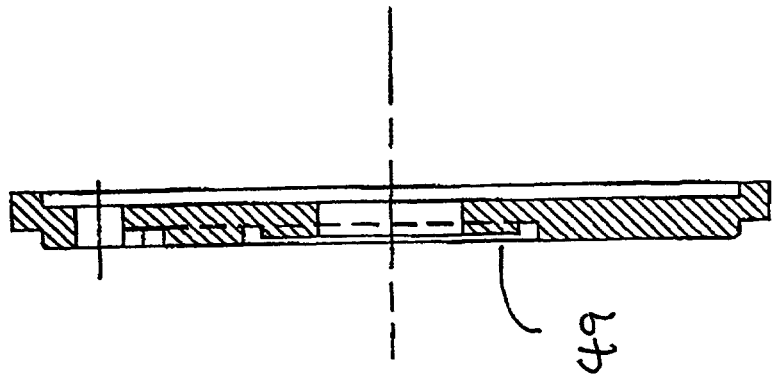
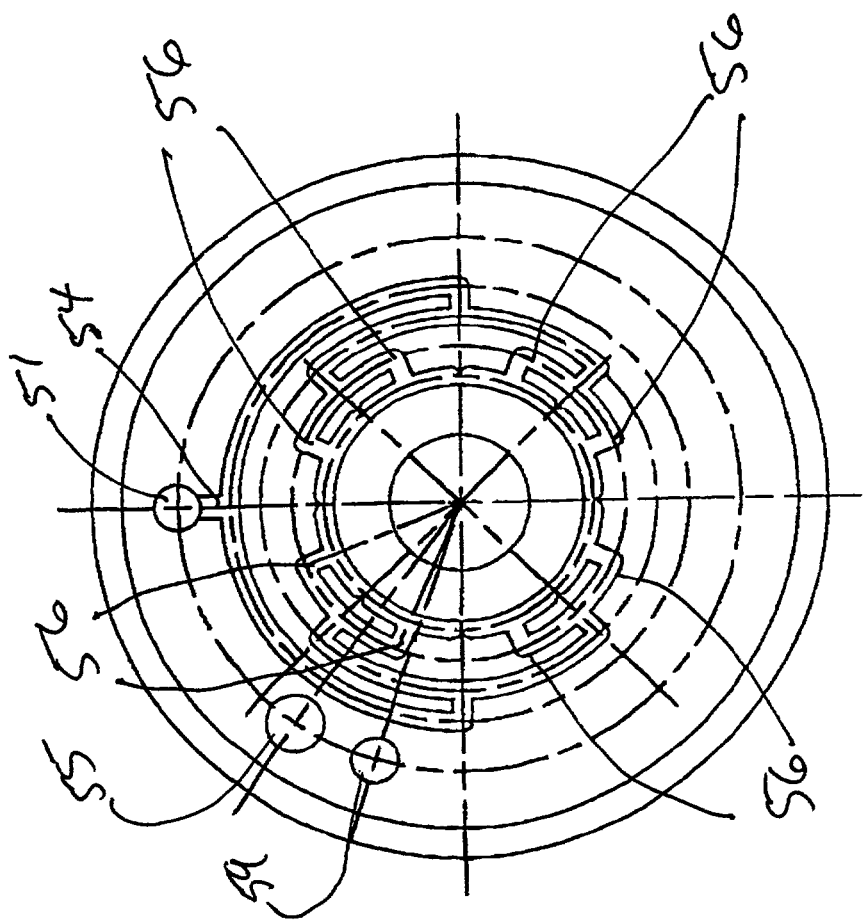
Fig. 5b

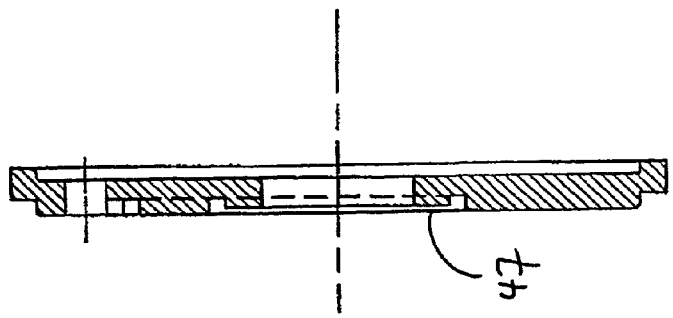
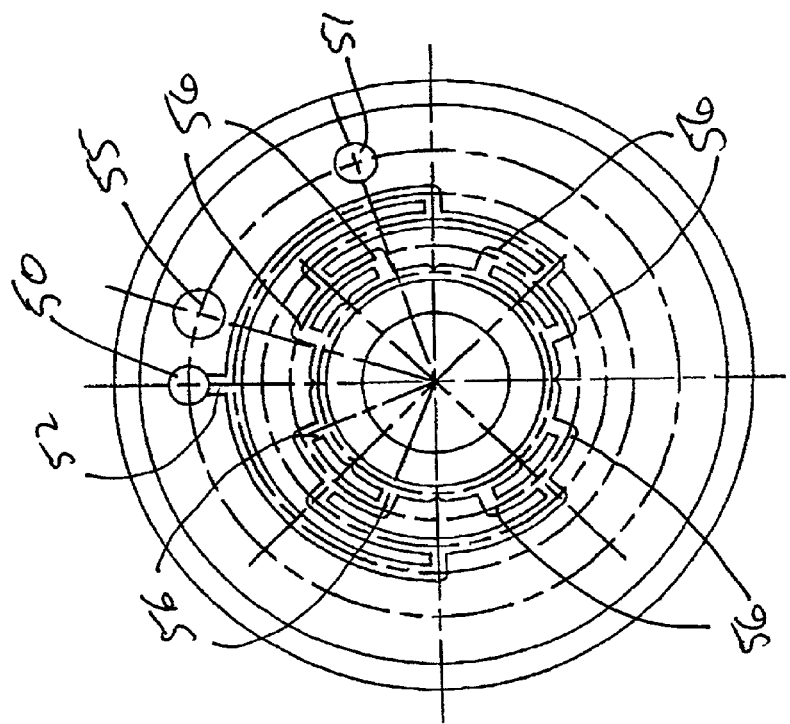
Fig. 5c

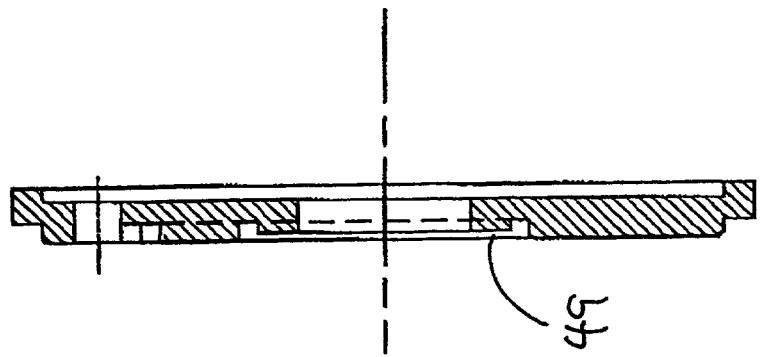
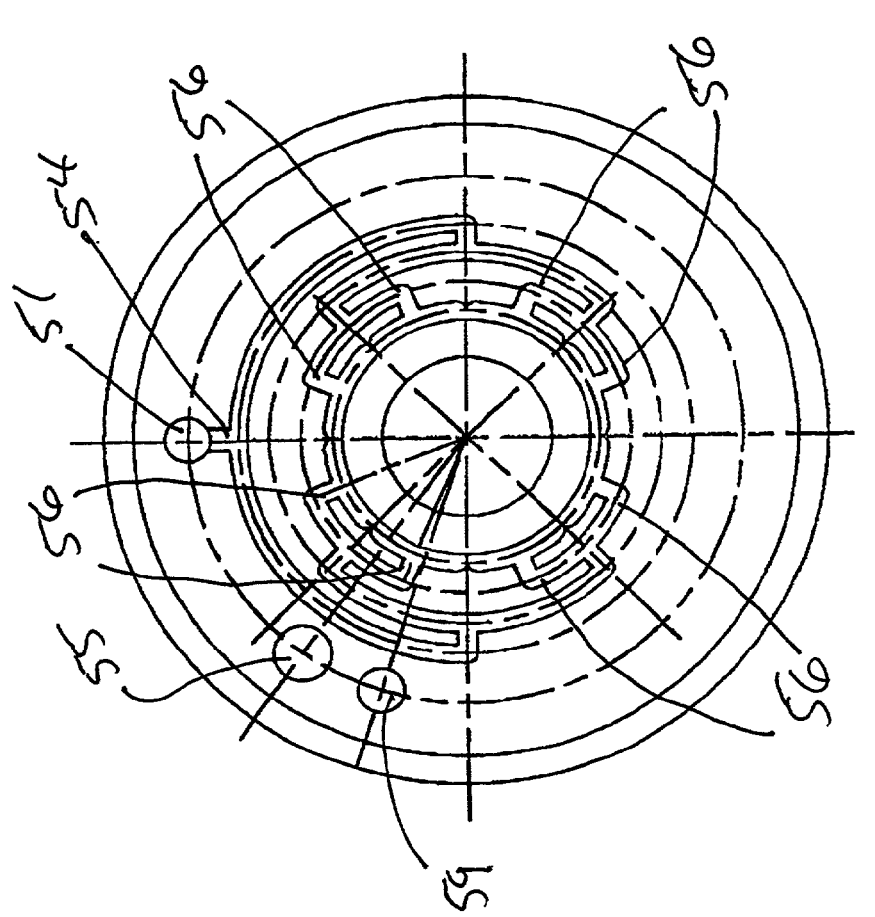
Fig 5d

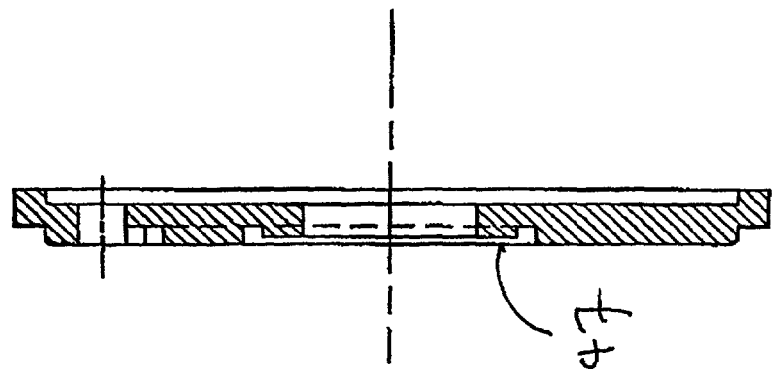
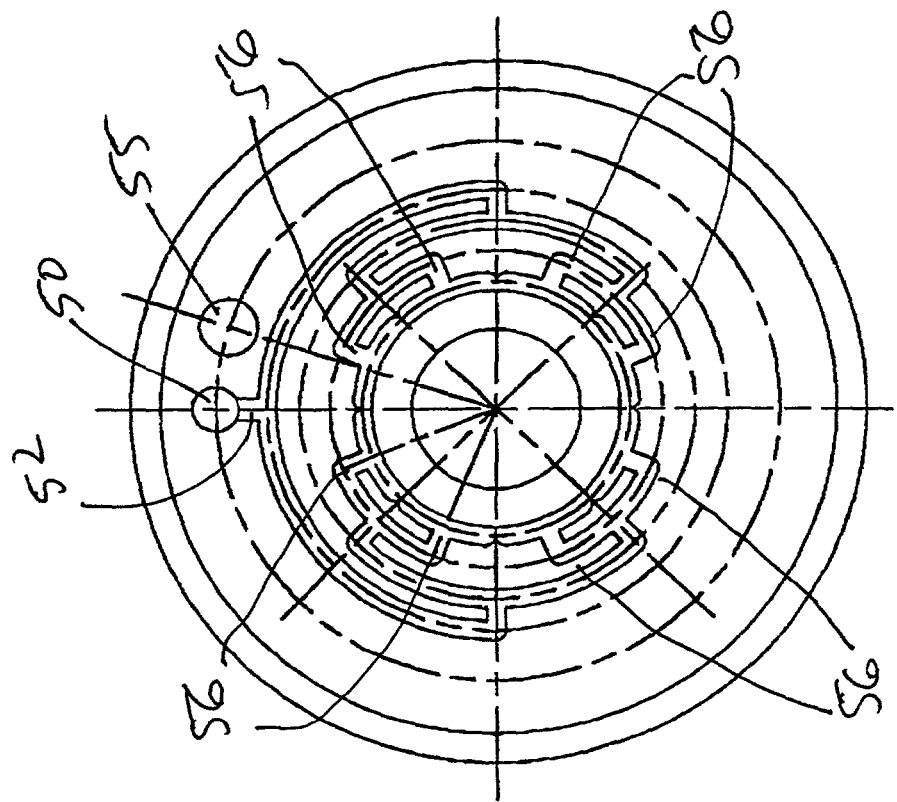
Fig 5e

MULTILAYER MEDICAL DEVICE

CROSS-REFERENCE TO RELATED APPLICATION

This application claims priority under 35 U.S.C. §120 to and is a continuation-in-part of commonly owned U.S. patent application Ser. No. 09/517,870, filed on Mar. 2, 2000, and entitled "Multilayer Medical Balloon," now abandoned, the entire contents of which are hereby incorporated by reference.

FIELD OF THE INVENTION

This invention relates to multi-layer medical devices.

BACKGROUND OF THE INVENTION

Many medical procedures utilize a balloon catheter to, for example, open an occluded lumen, as in angioplasty, position another medical implement, such as a stent or graft, or selectively block a passageway. In most cases, the balloon is positioned on the end of a long, narrow catheter shaft. The balloon is typically wrapped around the catheter shaft to reduce the radial profile for easier insertion. The catheter is then threaded through the body to position the balloon at a location of treatment and the balloon is inflated. Finally, the balloon is deflated and the catheter is withdrawn from the body.

SUMMARY

This invention relates to medical devices, such as medical tubing, e.g., catheter shafts, or medical balloons which have a wall composed of a plurality of layers formed of hard and soft polymers. In embodiments, the devices have, e.g., four, seven, thirteen, or twenty or more thin layers.

In an aspect, the invention features a medical device with at least four layers, including layers formed of hard polymer and layers formed of soft polymer.

In another aspect, the invention features a medical device including at least four layers formed of hard polymer and soft polymer. The soft polymer has a hardness of about 60 Shore D or less.

In another aspect, the invention features an extruded medical device including at least four polymer layers including layers of hard polymer and layers of soft polymer. At least one of the hard polymer layers has a thickness of about 0.1 micron or more.

In one aspect, the invention features a medical device that includes at least four layers. At least one layer is includes a liquid crystal polymer and a different polymer.

In another aspect, the invention features an extruded medical device that has at least four layers. At least one layer includes a liquid crystal polymer and a different polymer.

In yet another aspect, the invention features a medical device having four or more layers. Each layer has a thickness of from about 0.1 micron to about 10 micron. The device has a double wall thickness of from about 0.0001 inch to about 0.0015 inch In a further aspect, the invention features an extrusion apparatus for making a multilayer article. The apparatus includes two sections having a plurality of discs therebetween. Each of the discs has at least one passageway configured to permit fluid flow therethrough in a flow direction. The thickness of at least one of the discs in the flow direction is about one inch or less.

In another aspect, the invention features an extrusion apparatus for making a multilayer article. The apparatus includes two sections having a plurality of discs therebetween. At least one of the discs has at least two channels for forming a layer of the multi-layer article.

In another aspect, the invention features a medical coextruder and methods of extrusion involving delivering multiple polymers to an extrusion stream. The extrusion involves an assembly of delivery elements, wherein elements in the stream include inlet flow passages for directing a first polymer along the stream and outlet passages for delivering another polymer into the stream in a desired sequence. The elements are capable of assembly and reassembly to modify the sequence of delivery.

Embodiments may also include one or more of the following features.

The device includes at least five layers (e.g., at least six layers, at least seven layers, at least eight layers, at least nine layers, at least 10 layers, at least 11, layers, at least 12 layers, at least 13 layers, at least 20 layers) and/or no more than 100 layers (e.g., no more than 90 layers, no more than 80 layers, no more than 70 layers, no more than 60 layers, no more than 50 layers).

The hard layers have a total thickness of about 0.1 micron or greater (e.g., about 0.5 micron or greater, from about one micron to about 10 microns). The soft layers have a total thickness of about 0.05 micron or greater (e.g., from about 0.05 micron to about 5 microns).

The double wall thickness of the device is at least about 0.0001 inch (e.g., at least about 0.0005 inch, from about 0.0005 inch to about 0.006 inch, from about 0.0008 inch to about 0.004 inch, about 0.001 inch to about 0.003 inch, about 0.0022 inch, about 0.0015 inch).

The medical device is an extruded medical device.

The balloon has an inflated diameter of about 1.5 mm to about 6.0 mm.

The hard and soft layers alternate.

The hard polymer has a hardness greater than 60 Shore D and the soft polymer has a hardness of about 60 Shore D or less.

The hardness difference between adjacent layers is about 40 Shore D or less.

The soft polymer has a hardness of about 55 Shore D or less.

The device is about 30% (by thickness) or less of soft polymer and 70% (by thickness) or more of hard polymer.

The hard and/or soft polymer is a blend of polymers. The soft and hard polymer include block copolymers including common block moieties. The block moieties are amide segments and tretramethelyene glycol segments. The soft and/or hard polymer is selected from the group consisting of thermoplastic polyamides, and thermoplastic polyesters and thermoplastic elastomers. The soft and hard polymer include ester and ether segment block copolymers or polyurethane. The soft and/or hard polymer is biaxially oriented. The outermost layer is soft polymer.

The medical device is a tube or a balloon.

The balloon has a burst pressure of about 6 atm or more.

A 3 mm balloon can have a puncture force of about 50 g or more (e.g., about 75 g or more, about 90 g or more, about 95 g or more, about 100 g or more).

A 5 mm balloon can have a puncture force of about 100 g or more (e.g., about 1250 g or more, about 1500 g or more, about 1750 g or more, about 1800 g or more, about 1850 g or more).

The extruder delivery elements comprise a series of discs including flow channels formed in the face of the discs.

At least about one percent of the layers of the medical balloon can contain the liquid crystal polymer.

Embodiments of the apparatus can have one or more of the following features. The thickness of one or more discs (e.g., at least two discs, at least three discs, at least four discs, at least five discs, at least six discs, at least seven discs, at least eight discs, at least nine discs, at least 10 discs, at least 11 discs, at least 13 discs, at least 20 discs, etc., all the discs) in the flow direction can be about 0.75 inch or less (e.g., about 0.5 inch or less, about 0.4 inch or less, about 0.3 inch or less, about 0.2 inch or less, or about 0.15 inch or less). At least one of the discs (e.g., at least two discs, at least three discs, at least four discs, at least five discs, at least six discs, at least seven discs, at least eight discs, at least nine discs, at least 10 discs, at least 11 discs, at least 13 discs, at least 20 discs, etc., all the discs) can have at least two channels (e.g., at least three channels, at least four channels, at least five channels, at least six channels, at least seven channels, at least eight channels, etc.) for forming a layer of the multi-layer article.

Embodiments may include one or more of the following advantages. The use of a large number of thin layers distributes stresses, such as cracks, abrasions, etc., with the result that defects are less likely to propagate through the wall and lead to mechanical failure such as bursting. Thus, balloons exhibit enhanced burst strength, burst pressure and/or puncture resistance. The balloons may have thinner walls, while maintaining adequate burst pressure, burst pressure and/or puncture resistance. The balloons, particularly thinner-walled balloons, may be more easily folded about the catheter and more easily self-fold after deflation. The balloons have a softer, more compliant feel. Without increasing balloon wall thickness, the balloons can be more resistant to abrasion or puncture or cutting when used to deliver another implement, such as a stent or graft.

In certain embodiments, the apparatus used for co-extrusion can be relatively compact. This can be advantageous because it can reduce the residence time of the polymers in the apparatus during co-extrusion, thereby decreasing the likelihood that one or more of the layers will undergo substantial degradation during co-extrusion.

In certain embodiments, a multilayer article (e.g., a multilayer balloon or a multilayer tube), such as a multilayer article having one or more relatively thin layers, can exhibit good adhesion between at least two adjacent layers, good puncture resistance, high burst pressure, high burst strength, and/or good flexibility.

Still further features, aspects, and advantages, follow.

DESCRIPTION OF THE PREFERRED EMBODIMENT

We first briefly describe the drawings.

DESCRIPTION OF THE DRAWINGS

FIG. 1 is a side view of a balloon catheter;

FIG. 2 is a cross-section through a section of a single balloon side wall taken along the line 2-2 in FIG. 1;

FIG. 3a is a cross-sectional view of the first crosshead disc in FIG. 3 according to one embodiment;

FIG. 3b is a cross-sectional view of the second crosshead disc in FIG. 3 according to one embodiment;

FIG. 3c is a cross-sectional view of the third, fifth, seventh, ninth, and eleventh crosshead discs in FIG. 3 according to one embodiment;

FIG. 3d is a cross-sectional view of the fourth, sixth, eighth, tenth and twelfth crosshead discs in FIG. 3 according to one embodiment;

FIG. 3e is a cross-sectional view of the thirteenth crosshead disc in FIG. 3 according to one embodiment;

FIG. 3f is a cross-sectional view of assembly sections 26 and 28 according to one embodiment;

FIG. 3g is a cross-sectional view of assembly section 24 according to one embodiment;

FIG. 3h is a cross-sectional view of assembly section 22 according to one embodiment;

FIG. 3i is a cross-sectional view of a mandrel according to one embodiment;

FIG. 3j is a cross-sectional view of assembly section 30 according to one embodiment;

FIG. 3k is a cross-sectional view of the nozzle according to one embodiment;

FIG. 5a is a cross-sectional view of the first crosshead disc in FIG. 3 according to one embodiment;

FIG. 5b is a cross-sectional view of the second crosshead disc in FIG. 3 according to one embodiment;

FIG. 5c is a cross-sectional view of the third, fifth, seventh, ninth, and eleventh crosshead discs in FIG. 3 according to one embodiment;

FIG. 5d is a cross-sectional view of the fourth, sixth, eighth, tenth and twelfth crosshead discs in FIG. 3 according to one embodiment; and FIG. 5e is a cross-sectional view of the thirteenth crosshead disc in FIG. 3 according to one embodiment.

DESCRIPTION

Figure 3:
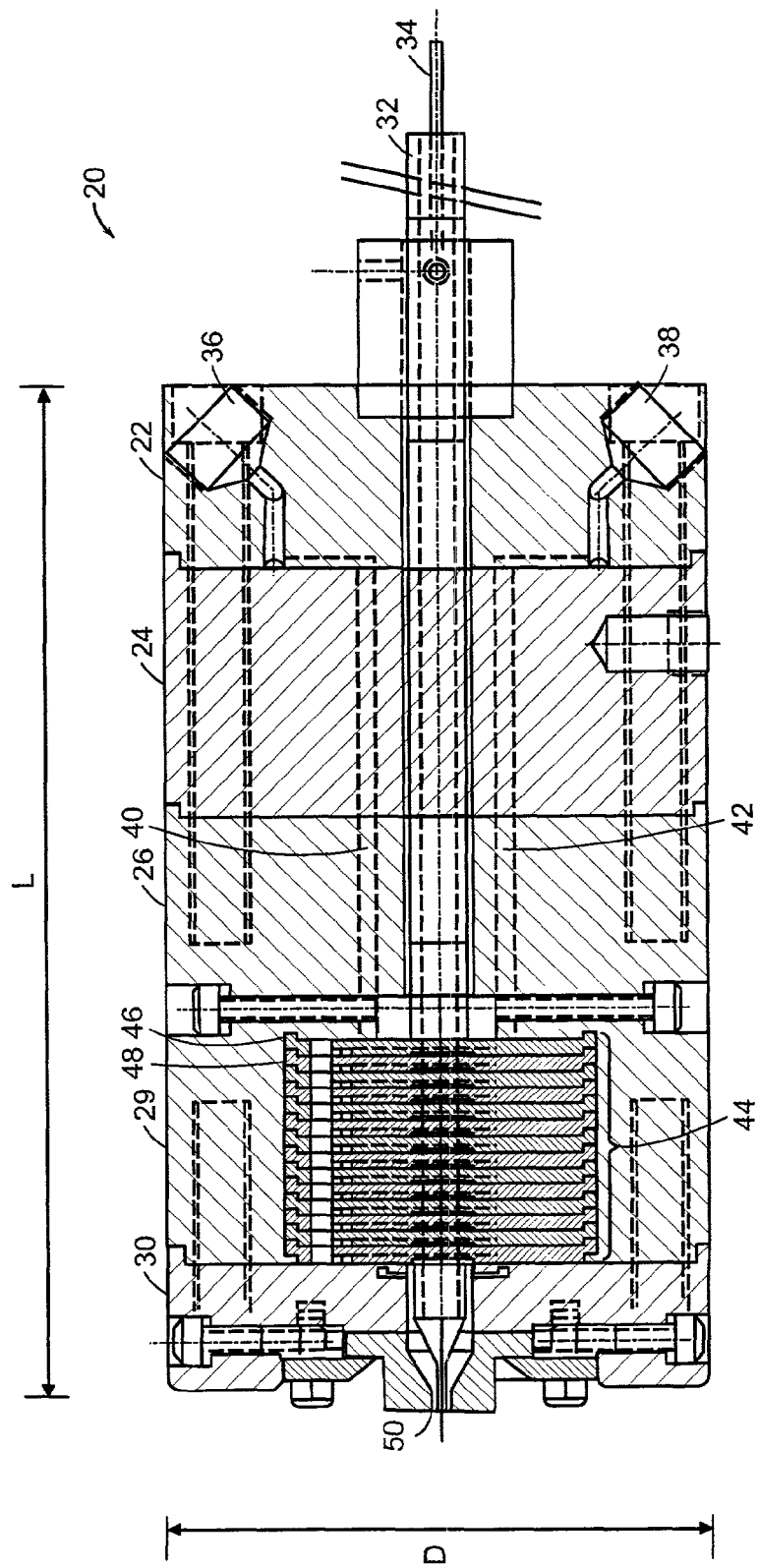
FIG. 3 is an assembly drawing of an extrusion crosshead.
Figure 31:
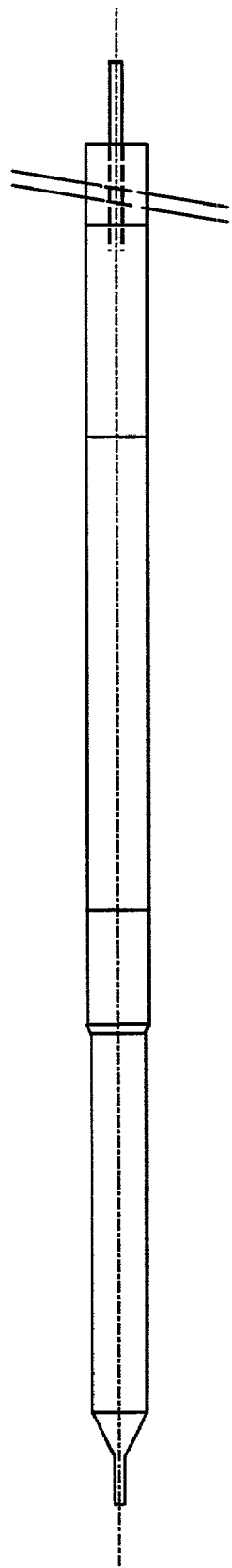

Referring to FIG. 1, a balloon catheter 2 includes a catheter shaft 4 which carries near its end an inflatable balloon 6. The catheter may be delivered over a guide wire 8 into, e.g., the coronary artery, to open an occluded area and/or deliver a stent. A suitable catheter system is described in, for example, Wang U.S. Pat. No. 5,195,969; Hamlin U.S. Pat. No. 5,270,086; and exemplified by the Ranger® system available from Boston Scientific Scimed, Maple Grove, Minn. Suitable stents and stent delivery is exemplified by the NIR on Ranger® system, available from Boston Scientific Scimed, Maple Grove, Minn. The entire contents of all of the patents above are incorporated herein by reference. The catheter shaft may also be a multilayer tube formed by the techniques described below.

Referring as well to FIG. 2, the balloon wall 10 is formed of multiple, in this example seven, thin layers, 12, 13, 14, 15, 16, 17, 18. The multitude of thin layers distributes stresses and defects, such as cracks or punctures, so that they are less likely to propagate through the wall to the point of causing a failure. The layers are thicker than the typical size of defects, e.g., gas bubbles formed in the extrusion or foreign particles.

In certain embodiments, one or more layers (e.g., one or more layers of a balloon) can have a minimum thickness of at least about 0.02 micron (e.g., at least about 0.05 micron, at least about 0.1 micron, at least about 0.25 micron, at least about 0.5 micron, at least about 0.75 micron, at least about one micron, at least about 1.5 microns, at least about 2 microns, at least about 2.5 microns, at least about 3 microns, at least about 3.5 microns) and/or a maximum thickness of at most about 20 microns (e.g., at most about 15 microns, at most about 10 microns, at most about nine microns, at most about eight microns, at most about seven microns, at most about six microns, at most about five microns, at most about four microns, at most about three microns, at most about two microns, at most about one micron, at most about 0.5 micron, at most about 0.25 micron).

Typically, the hard layers have a total thickness of about 0.1 micron or greater (e.g., about 0.5 micron or greater, from about one micron to about 10 microns). Typically, the soft layers have a total thickness of about 0.05 micron or greater (e.g., from about 0.05 micron to about 5 microns).

The number of layers is generally greater than one (e.g., at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, etc. layers). In certain embodiments, the number of layers is less than 100 (e.g., less than 90, less than 80, less than 70, less than 60, less than 50, less than 40, less than 35, less than 30, less than 25, less than 20, less than 15, less than 10). The number of layers is preferably four or greater and may be, for example, seven, thirteen, twenty or more. Typically no more than about 50 layers are used for balloons of conventional wall thicknesses, but greater than 50 layers is also possible in embodiments.

Different layers are formed of different hardnesses which assist distribution of stress and retard defect propagation, while still providing high burst strength and low distention. Preferably, layers may be formed of hard polymer that has a hardness of more than about 60 Shore D, preferably 65 Shore D or more, and softer polymer that has a hardness of about 60 Shore D or less. In some embodiments, the soft polymer can have a hardness of greater than about 60 Shore D, but it is still softer than the hard polymer. It is often desirable that the difference in hardnesses of adjacent bonded layers is about 40 Shore D or less, preferably 20 Shore D or less, which enhances compatibility between the layers and reduces delamination at the interface. Hardness may be measured according to ASTM D2240. The layers can alternate between hard and soft polymer. The layers may be of progressively increasing hardness. For example, the layers may be of progressively increasing hardness from the outermost layer to the inner most layer. Preferably, for stent delivery, the outermost layer is a soft layer, which absorbs and distributes stress and abrasion imposed by the stent.

The thickness of the soft and hard layers may be different or the same. In some embodiments, the soft layers make up from about one percent to about 45% (e.g., from about 5% to about 45%, from about 5% to about 40%), about 30% or less, from about 20% to about 30%) of the total tube or balloon wall thickness and hard polymer makes up the balance. In certain embodiments, the hard layers make up from about one percent to about 45% (e.g., from about 5% to about 45%, from about 5% to about 40%, about 30% or less, from about 20% to about 30%) of the total tube or balloon wall thickness and hard polymer makes up the balance. As a result, for a device with a comparable number of soft and hard layers, the soft polymer layers may be thinner or thicker than the hard polymer layers. The thickness of the layers may vary progressively. For example, the layers may get thicker from the outermost layer to the innermost layer or vice versa. The thickness of the layers of one type (soft or hard) may vary while the layers of the other type are constant.

The layers may be of substantially pure polymer or they may be blends of different polymers. All of the soft (or hard) layers may be made of the same soft (or hard) polymer or the different soft (or hard) layers may be made of different polymers. Preferably, the soft and hard are made of block copolymers including common block moieties, which enhances compatibility, while maintaining defect retardation. For example, the block moieties may be amide segments and tetramethylene glycol segments. A preferred example is the Pebax family of polymers available from ElfAtoChem, Philadelphia, Pa. which can be used pure or as blends. For example, Pebax 5533 (55 Shore D) can be blended with Pebax 2533 (25 Shore D) in a weight ratio of about 4 to 1 to provide a soft polymer of about 50 Shore D. Another preferred combination of hard and soft polymers is polybutylene terephthalate (PBT) such as Celanex (over 80 Shore D, from Ticona, Summit, N.J.) and polyester/ether block copolymer available as Arnitel (55 Shore D, from DSM, Erionspilla, Ind.). A further preferred combination of hard and soft polymers is PBT and one or more PBT thermoplastic elastomers, such as Riteflex (55 Shore D from Ticona in Summit, N.J.) and Hytrel (55 Shore D from E. I. Dupont de Nemours, Wilmington, Del.) for example. Still another preferred combination of hard and soft polymers is polyethylene terephthalate (PET) and a thermoplastic elastomer, such as a PBT thermoplastic elastomer (e.g., Arnitel, Hytrel, or Riteflex).

In certain embodiments, one or more layers can contain one or more nylons. For example, one or more of the hard polymer layers can contain one or more nylons. For example, a preferred combination of hard and soft polymers is a nylon and a Pebax-type material, such as Pebax, Grilon, Grilamid (EMS) and/or Vestamid (Creanova). Examples of nylons include aliphatic nylons, such as Nylon 11 (Elf Atochem), Nylon 6 (Allied Signal), Nylon 6/10 (BASF), Nylon 6/12 (Ashley Polymers) and Nylon 12. Additional examples of nylons include aromatic nylons, such as Grivory (EMS) and Nylon MXD-6. Other nylons and/or combinations of nylons can be used.

In some embodiments, one or more layers can contain a liquid crystal polymer (LCP) (e.g., a composite material having the LCP incorporated therein). Examples of LCP's include polyester(s), polyamide(s) and/or their copolymers, such as Vectra A (Ticona), Vectra B (Ticona) and Vectra LKX (Ticona) (e.g., Vectra LKX 1111 (Ticona)). Other LCPs and/or combinations of LCPs can be used.

The LCP can be incorporated into one or more polymers, such as, for example, a Pebax-type material, a nylon, a thermoplastic polyester and/or thermoplastic elastomer versions thereof. In certain embodiments, the liquid crystal polymer can be incorporated into one or more of the polymer layers to form a hard layer of material (e.g., a layer of material with more than about 60 Shore D hardness, such as more than about 65 Shore D hardness). In a preferred combination, LCP is incorporated into a layer containing one or more Pebax-type materials, such as Pebax, Grilon, Grilamid and/or Vestamid. In certain embodiments, an LCP-containing composition can be relatively stiff in the direction of melt flow. Without wishing to be bound by theory, it is believed that this may result because LCP crystals (e.g., fibers) form or align in the melt flow direction as the polymer composite cools from a liquid state to a solid state. It is believed that the LCP fibers can reinforce the other polymer(s) contained in the layer (e.g., matrix polymer(s)), which can restrict a balloon from growing in length during inflation while, depending on the LCP content in the composite material, permitting the balloon to be inflated.

The amount of LCP contained in the tube or balloon can vary depending upon its intended use. In some embodiments, as the percentage of LCP in a composite material is decreased, the individual layer thickness and the overall thickness of one or more layers of an LCP-containing composite material in a balloon or tube can be increased.

Generally, the LCP content of a tube or balloon can at least about 0.1 weight percent, such as from about 0.1 weight percent to about 20 weight percent (e.g., from about 0.5 weight percent to about 10 weight percent, from about one to about five weight percent). Within a given layer, the LCP content can be at least about 0.1 weight percent (e.g., from about one weight percent to about 50 weight percent, from about five weight percent to about 20 weight percent, from about five weight percent to about 15 weight percent).

Typically, the percentage of layers containing LCP relative to the total number of layers can be from about one percent to about 80 percent (e.g., at least about five percent, at least about 10 percent, at least about 15 percent, at least about 20 percent, at least about 25 percent, at least about 30 percent, at least about 35 percent, at least about 40 percent, at most about 80 percent, at most about 75 percent, at most about 70 percent, at most about 65 percent, at most about 60 percent, at most about 55 percent, at most about 50 percent, at most about 45 percent).

In certain embodiments, an adhesion enhancing material can be incorporated into one or more material layers. An adhesion enhancing material can be used, for example, to enhance the adhesion between adjacent layers. Examples of adhesion enhancing materials include epoxy or anhydride modified polyoloefins, such as Lotader (Elf Atochem) and Kodar PETG (Eastman Kodak). Typically, an adhesion enhancing material is added to a material (e.g., a composition containing one or more polymers) prior to extrusion. For example, in embodiments in which alternate layers are formed of PET and PBT, PETG can be added to the PET before extrusion.

The amount of adhesion enhancing material can vary depending upon the intended use. In some embodiments, a sufficient amount of adhesion enhancing material(s) are included in the material so that the adhesion enhancing material(s) makes up at least about 0.5 percent of the resulting mixture that forms the layer (e.g., at least about one percent, at least about five percent, at least about 10 percent) and/or at most about 20 percent of the resulting mixture that forms the layer (e.g., at most about 15 percent, at most about 12 percent, at most about 10 percent).

In certain embodiments, the adhesion between one or more adjacent layers can vary as layer thickness is varied. Generally, embodiments can provide adhesion between one or more (e.g., all) layers in a medical device (e.g., a balloon or tube). For example, one or more (e.g., all) layers in a medical device (e.g., a balloon or tube) can demonstrate good adhesion when flexed, deflated and/or inflated. In some embodiments, a medical device (e.g., a balloon or tube) can show good flexibility and/or adhesion (e.g., when one or more layers are relatively thin).

In some embodiments, a compatibilizing material can be incorporated into one or more material layers. The compatiblizing material can be designed, for example, to modify one or more phase boundaries of the LCP(s) and one or more of the other polymer(s) (e.g., thermoplastic polymer(s)) and/or to enhance adhesion between the LCPs and one or more of the other polymer(s). The compatibilizing material can be a copolymer, such as a block copolymer, including moieties of at least two different chemical structures, respectively providing compatibility with an LCP and one or more other polymers in the mixture. The compatibiling material can be a reactive polymer that reacts with the LCP and/or one or more other polymers in the mixture. The compatibilizing material can be a catalyst that promotes a reaction between the LCP and one or more other polymers in the mixture. Other compatibilizing materials can be used. Combinations of compatibilizing materials can be used.

Examples of compatibilizing materials include copolyester elastomers, ethylene unsaturated ester copolymers, such as ethylene-maleic anhydride copolymers, copolymers of ethylene and a carboxylic acid or acid derivative, such as ethylene-methyl acrylate copolymers, polyolefins or ethylene-unsaturated ester copolymers grafted with functional monomers, such as ethylene-methyl acrylate copolymers, copolymers of ethylene and a carboxylic acid or acid derivative, such as ethylene-methyl acrylate maleic anhydride terpolymers, terpolymers of ethylene, unsaturated ester and a carboxylic acid or acid derivative, such as ethylene-methyl acrylate-methacrylic acid terpolymers, maleic acid grafted styrene-ethylene-butadiene-styrene block copolymers, and acrylic acid elastomers, such as acrylic rubbers. Similar polymers containing epoxy functional groups, for instance derived from glycidyl methylacrylate (e.g., alkyl(meth)acrylate-ethylene-glycidyl (meth)acrylate polymers) can be used. Ionomeric copolymers can be used. PETG can be used. Examples of compatibilizing materials include Hytrel HTR-6108, Polybond 3009 (BP Chemicals), SP 2205 (Chevron), DS 1328/60 (Chevron), Lotader 2400, Escor ATX-320, Escor ATX-325, Vamac G1 and Lotader AX8660. In certain embodiments, a compatibilizing material (e.g., PETG) can be mixed with one or more polymers (e.g., an LCP-containing material) prior to extrusion.

There are many ways in which LCPs can be blended into thermoplastics. The LCP blend can be a ternary system of LCP, thermoplastic and compatibilizing materials. Systems with multiple combinations of different LCPs, different thermoplastics and different compatibilizing materials are contemplated.

The compatibilized blend can be a blend of polyazomethine LCP, a thermoplastic polymer such as a polyamide, and a compatibilizing material such as a caprolactum having at least one functional group capable of showing compatibility and/or reactivity to the LCP and/or the thermoplastic polymer. Such blends are described, for example, in U.S. Pat. No. 5,565,530, which is hereby incorporated by reference.

One polymer blend product which can be used include PET, a wholly aromatic LCP copolyester and an ethylene-methyl acrylate-acrylic acid terpolymer compatibilzing material, such as, for example, Escor ATX320, Escor ATX325, or Escor XV-11.04. Another polymer blend product includes PET, a wholly aromatic LCP copolyester and an ethylene-maleic anhydride copolymer compatibilizing material, such as Polybond 3009. Another polymer blend product includes PET, a wholly aromatic LCP copolyester and an ethylene-methyl acrylate copolymer grated with maleic anhydride compatibilizing material, such as DS 1328/60, or a copolyester elastomer, such as Hytrel HTR 6108.

Polymer blend products including PET, LCP and at least two compatibilizing materials can be used. For example, DS 1328/60 and Polybond 3009 can be used with the LCP Vectra. As an additional example, when the LCP is Vectra, the compatibilizing materials can be Polybond 3009 and at least one additional compatibilizing material selected from Escor ATX-320, Escor ATX-325, DS 1328160, Escor XV-11.04 and Hytrel HTR-6108.

In certain embodiments, consideration is given to the properties of the LCP and the other polymer(s) (e.g., PET), as well as the desired properties of the resulting blend, when selecting the compatibilizing material(s).

In some embodiments containing an LCP, a thermoplastic polymer and compatibilizing material(s), the blend product includes from about 0.1 weight percent to about 10 weight percent (e.g., from about 0.5 weight percent to about 2 percent) LCP, from about 40 weight percent to about 99 weight percent (e.g., from about 85 weight percent to about 99 weight percent) thermoplastic polymer, and from about 0.1 weight percent to about 30 weight percent (e.g., from about one weight percent to about 10 weight percent) compatibilizing material(s).

While certain polymers and polymer combinations are discussed above, other polymers and polymer combinations can also be used. Other polymers include, for example, elastomers such as thermoplastic elastomers and engineering thermoplastic elastomers, such as polybutylene terephthalate-polyethene glycol block copolymers, which are available, for example, as Hytrel. These are discussed in Hamilton U.S. Pat. No. 5,797,877, the entire content of which is incorporated herein by reference. Other polymers include polyurethenes. Other polymers include copolymers such as ABS (acrylonitrile-butadiene-styrene), ABS/nylon, ABS/-polyvinyl chloride (PVC), ABS/polycarbonate, acrylonitrile copolymer, polyacrylamide, polyacrylate and polyacrylsulfone, polyesters such as polyethylene terephthalate (PET), polybutylene terephthalate (PBT), polyethylene naphthalate (PEN), liquid crystal polymer (LCP), polyester/polycaprolactone and polyester/polyadipate; and high melt temperature polyethers including polyetheretherketone (PEEK), polyethersulfone (PES), polyetherimide (PEI) and polyetherketone (PEK), polymenthylpentene, polyphenylene ether, polyphenylene sulfide, and styrene acrylonitrile (SAN), polyamides such as nylon 6, nylon 6/6, nylon 6/66, nylon 6/9, nylon 6/10, nylon 6/12, nylon 11, nylon 12, ethylene, propylene ethylene vinylacetate and ethylene vinyl alcohol (EVA), various ionomers, polyethylene type I-IV, polyolefins, polyurethane, polyvinyl chloride, and polysiloxanes (silicones). Those with low to medium melt temperatures include fluorocarbons such as polychlorotriethylene (CTFE), poly[ethylene-co-chlorotrifluoroethylene] (ECTFE) copolymer ethylene tetrafluoroethylene (ETFE), copolymer tetrafluoroethylene and hexafluoropropylene (FEP), perfluoroalkane (PFA) and poly[vinylidene fluoride] (PVDF).

The overall wall thickness of the tube or balloon and the inflatable diameter of the balloon are based on the medical application. Preferably, the balloons have a double wall thickness (twice the nominal thickness through a single sidewall of the balloon) of at least about 0.0001 inch (e.g., at least about 0.0005 inch, from about 0.0005 inch to about 0.006 inch, from about 0.0008 inch to about 0.004 inch, about 0.001 inch to about 0.003 inch, about 0.0022 inch, about 0.0015 inch) for inflatable diameters of about 1.5 mm to about 6.0 mm. Smaller diameter balloons typically have the thinner walls.

For certain PTCA balloons, the inflation diameter is about 1.5 mm to about 6 mm and the burst pressure (99% burst) about 12 atmosphere or greater. For certain peripheral angioplasty balloons, the diameter is about 5 mm to about 30 mm and burst pressure is about 6 atmospheres or more. The balloons can also be used in non-vascular applications, such as gastrointestinal and esophageal applications. Burst pressure may be measured by a burst station that is equipped with a pressure and vacuum cycle controller and a 37° C. water bath. Burst strength is calculated by P(D)/2T where P is the burst pressure, D the nominal balloon diameter, and 2T initial balloon double-wall thickness. In some embodiments, a PTCA balloon has a burst strength that, when measured according to this test, is at least about 10,000 psi (e.g., from about 14,000 psi to about 40,000 psi, from about 20,000 psi to about 40,000 psi, from about 25,000 psi to about 40,000 psi, about 28,000 psi). In certain embodiments, a peripheral angioplasty balloon has a burst strength that, when measured according to this test, is at least about 10,000 psi (e.g., from about 18,000 psi to about 50,000 psi, from about 25,000 psi to about 50,000 psi, from about 30,000 psi to about 40,000 psi, about 36,000 psi).

In some embodiments, increasing the number of layers can increase the puncture resistance of a balloon or tube. For example, the puncture resistance of a balloon having four layers can be higher than a balloon having the same material make up (i.e., the same percentage of each chemical component, such a polymer and/or an additive) and the same double thickness but formed of two layers. In certain embodiments, a balloon having more than three layers (e.g., four layers, five layers, six layers, seven layers, eight layers, nine layers, 10 layers, 11 layers, 12 layers, 13 layers, 20 layers, etc.) can have a puncture resistance that is at least about three percent higher (e.g., at least about five percent, at least about 10 percent, at least about 20 percent, at least about 30 percent) higher than a balloon having less than three layers (e.g., one layer, two layers or three layers) that has the same material make up and the same double wall thickness as the balloon having more than three layers.

Typically, tubes and/or balloons are prepared by an extrusion process. Generally, this process can involve the use of an extrusion apparatus (e.g., a crosshead, such as a compact crosshead) having a series of discs. For example, the apparatus can have one disc per material layer. Each disc can have one or more channels (e.g., one channel, two channels, three channels, four channels, five channels, six channels, seven channels, eight channels, 10 channels, 12 channels, 14 channels, 16 channels, etc.). In some embodiments, it can be desirable to have a relatively large number of channels (e.g., five, six, seven, eight, etc. channels) in at least one disc (e.g., in one disc, two discs, three discs, four discs, five discs, six discs, seven discs, eight discs, etc.) to enhance the degree of circularity of the layers in the balloon. In some embodiments, each disc has a relatively large number of channels. The number of channels can be selected based upon, for example, the volumetric output, the temperature, the viscosity, the pressure drop, the outer diameter of the discs, the material (e.g., polymer(s)) used, and/or the channel dimensions.

In certain embodiments, the thickness of one or more of the discs (e.g., at least two discs, at least three discs, at least four discs, at least five discs, at least six discs, at least seven discs, at least eight discs, at least nine discs, at least 10 discs, at least 11 discs, at least 12 discs, at least 13 discs, at least 20 discs, etc., each disc) can be less than about one inch (e.g., less than about 0.75 inch, less than about 0.5 inch, less than about 0.4 inch, less than about 0.3 inch, less than about 0.2 inch, less than about 0.15 inch, less than about 0.1 inch, less than about 0.05 inch) in the direction parallel to the flow of material (polymer) through the apparatus (e.g., in the direction L shown in FIG. 3).

In some embodiments, an apparatus has a 13 disc stack having a total thickness of less than about 13 inches (e.g., less than about 12 inches, less than about 11 inches, less than about 10 inches, less than about nine inches, less than about eight inches, less than about seven inches, less than about six inches, less than about 5.5 inches, less than about five inches, less than about 4.5 inches, less than about four inches, less than about 3.5 inches, less than about three inches, less than about 2.5 inches, less than about two inches, less than about 1.9 inches, less than about 1.8 inches) in the direction parallel to the flow of material (polymer) through the apparatus (e.g., in the direction L shown in FIG. 3).

In certain embodiments, an apparatus has a 20 disc stack having a total thickness of less than about 20 inches (e.g., less than about 19 inches, less than about 18 inches, less than about 17 inches, less than about 16 inches, less than about 15 inches, less than about 14 six inches, less than about 13 inches, less than about 12 inches, less than about 10 inches, less than about 9.5 inches, less than about nine inches, less than about 8.5 inches, less than about eight inches, less than about 7.5 inches, less than about seven inches, less than about 6.5 inches, less than about 6.4 inches, less than about 6.3 inches, less than about 6.2 inches, less than about 6.1 inches, less than about six inches) in the direction parallel to the flow of material (polymer) through the apparatus (e.g., in the direction L shown in FIG. 3).

FIG. 3 shows a cross-sectional view of an embodiment of an extrusion apparatus (a compact crosshead) 20 that can be used in the preparation of a 13 layer balloon or tube. The tubes and balloons may be formed by first coextruding a multi-layer tube having the desired sequence of layers. Compact crosshead 20 that includes a series of assembly sections 22, 24, 26, 28, 30 with a common bore into which is placed a spacing mandrel 32 that encompasses an air supply tube 34. The assembly sections 22, 24, 26 define inlets 36, 38 from separate extruders (not shown) which feed different polymers (in this example polymer A and polymer B) into the head and include passageways 40, 42 which direct the polymers to assembly section 28.

Assembly section 28 houses a series 44, in this example thirteen, extrusion discs. Each of the discs include passageways for both polymers but an extrusion inlet and outlet for only one of the polymers. (An exception is the last disc which includes a passageway for only one polymer.) In this way, the polymer flow continues along the assembly but each polymer is added to the extrusion stream in the desired order. In this example, every other disc has an inlet and outlet for the first polymer and every other intervening disc has an inlet and outlet for the second polymer.

Figure 4:
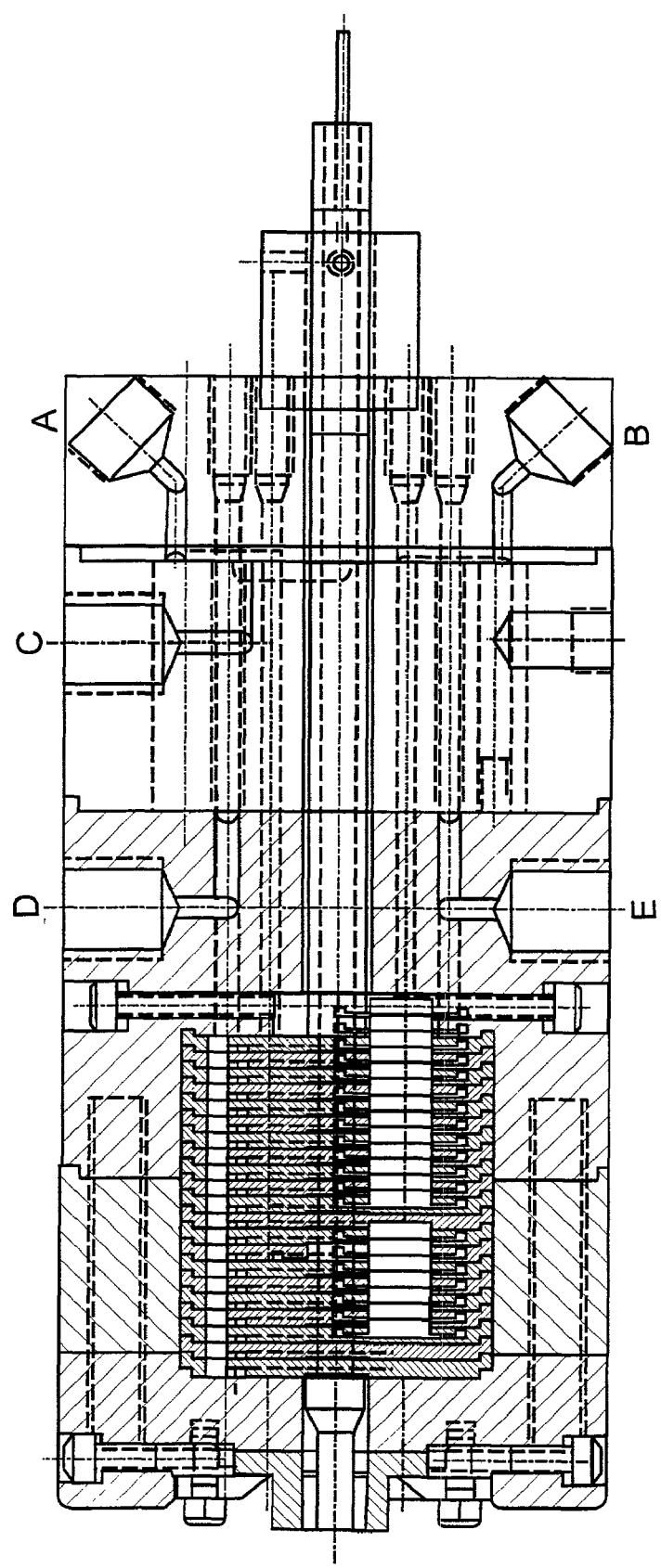
FIG. 4 is an assembly drawing of a crosshead arrangement according to an embodiment.

FIGS. 3a-3e show five different four channel disc designs that can be used together in crosshead 20. The inlets and outlets of the discs are formed as machined channels in the face of the discs. Polymer A flows through a passageway 50 and polymer B flows through a passageway 51. (An opening 55 for an alignment pin is provided for registration of the discs.) The outlets are formed by channels 56 that lead to gaps between adjacent discs. For example, the first disc 46 has an inlet 52 and an outlet 47 for the first polymer and passageway 51 for the second polymer but no inlet or outlet for the second polymer. The second disc 48 has an inlet 54 and an outlet 49 for the second polymer and a passageway 59 for the first polymer but no inlet or outlet for the first polymer. As a result, the first polymer will be deposited as the innermost layer, the second polymer as the next adjacent layer, the first polymer will be the third layer and so on. At the end of the thirteenth disc a thirteen layer extrusion in which alternate layers of different polymers is achieved. The thirteenth disc (FIG. 3e) is formed without passageway 51. The extrusion is sized to the desired diameter at the nozzle 50 on assembly section 30. The crosshead provides for substantial flexibility in a compact design by changing the discs or outlet configurations of the discs to obtain a desired sequence of layers. As illustrated in the mechanical drawings, the diameter of the central opening in the discs can vary to facilitate polymer delivery along the stream. In addition, the channels can be arranged to direct polymer(s) into the stream at different radial orientations in successive discs. The number of layers can be varied from a single layer, two layers, three layers or more layers by controlling the number of discs. Referring as well to FIG. 4, a twenty disc arrangement, the system can as well be adapted for coextruding a greater number of polymers by replacing sections 24, 26, with sections that include additional extruder inlets and configuring the discs to include channels to accommodate the flow of the additional polymers. In the embodiment of FIG. 3, the assembly sections and the discs are formed of stainless steel and the system has an overall diameter, D, of about 3.5 inch and an overall length, L, of about 6.5 inch. The extruders may be one inch Brabrender extruders (N J). For an example of a tubing with thirteen total layers with alternating layers of hard and soft polymer the system may be operated as follows. The hard polymer is Pebax 7033 with the extruder including eight zones, the first three temperature zones are heated to 340° F., 365 F., and 385° F., and the remaining five zones to 395° F. The soft polymer is a blend of 85% Pebax 5533/15% Pebax 2533 (weight percent) with the first zone at 345° F. and the remaining zones at 365° F. The crosshead is heated to 395° F. with a heater band. The ratio of feed rate of the hard polymer to the feed rate of the soft polymer is about 4:1. The first layer (innermost) is soft polymer and the tube therefore has seven soft layers and six hard layers. The line speed is about 47.3 ft/min. The resulting tubing has a single wall thickness of 0.008 inch, an OD of about 0.0348 inch, and an ID of about 0.0184 inch. Tubing formed by these processes can be used as medical tubing, e.g., as catheter shafts or polymer guide wires, or it may be processed to form a multilayer medical balloon.

FIGS. 5a through 5e show five different eight channel disc designs that can be used together in crosshead 20 in a manner similar to that described above with respect to the four channel discs shown in FIGS. 3a through 3e. As shown in FIGS. 5a through 5e, however, these discs each have eight channels 56. This can result in the velocity of the polymer flow at outlet 47 being more uniform around the perimeter of outlet 47, thereby promoting circularity of individual layers in a tube and/or balloon, and/or increasing circularity of the interfaces between layers in a tube and/or balloon. The eight channel pattern can be machined into the same size discs as the four-channel pattern so that the four and eight channel discs may be used with the same extrusion equipment. In certain embodiments, the width of the disc material between the channels generally constrains their size and location on the discs. For example, in some embodiments, discs machined from 440C stainless steel may maintain a minimum width between channels of about 0.035 inches without cracking under the pressure of the extruded polymer.

In some embodiments, the disc design described herein can provide an advantage of allowing for control of the individual layer thickness. Thus, by manipulating the disc design, the thickness of a given layer can be changed and/or controlled.

To form a balloon, the tube is necked by a stretching machine at room temperature and then the necked tube is inserted into a balloon mold of the desired diameter with the necking transition located at the cone area of the mold (the unstretched portion is formed into balloon body section). After the tubing section is securely inside the mold, the mold is placed in a fixture. The tubing section extends out the top of the mold and is fed into a Touhy clamp through which nitrogen gas applied to the inner lumen of the tubing at forming pressure, with tension 60 grams applied to the tubing. The tubing section at the bottom of the mold is clamped off such that the pressure is maintained inside the tubing section. The mold is then gradually dipped into a deionized hot water bath maintained at about 950° C. (±1° C.) to a point just above the proximal waist portion of the mold at a controlled manner. A balloon is formed by radial expansion with internal pressure. After the balloon is formed, the mold is removed from the hot water bath and cooled for approximately 10 sec in a deionized water bath maintained at 10° C. Other processes can be used to form multi-layer balloons or tubes including dipping or spraying layers or fusing separately extruded concentrically arranged tubes.

The following examples are illustrative only and not intended as limiting. The multilayer tubes and balloons described in the examples were extruded using an a four channel apparatus.

Example 1

A thirteen layer tubing was formed by coextruding Pebax 7033 and mixture of Pebax 5533 (85% by weight) and Pebax 2533 (15% by weight) in an alternate layer structure. A soft layer of Pebax 5533/Pebax 2533 mixture was the outermost layer. The material (by thickness) ratio of Pebax 7033 to the mixture was about 4 to 1. Four 3.25 mm balloons were made from tubing of 0.0170 ID×0.0342 OD (inch). The balloons were formed at 95° C. and 515 psi forming pressure. The balloons had a double wall thickness of 0.00150 inch. The soft polymer layers were about 0.54 micron thick. The hard polymer layers were about 2.54 micron thick. The balloon burst at about 309 psi and calculated burst strength was about 26,250 psi.

Example 2

A seven layer tubing was coextruded with Pebax 7033 and Pebax 5533 in an alternate layer structure. A soft layer of Pebax 5533 was the outermost layer. The material ratio (by thickness) of Pebax 7033 to Pebax 5533 was about 4 to 1. Four 3.0 mm balloons were made from tubing of 0.0200 ID×0.0330 OD (inch). The balloons were formed at 95° C. and at 360 psi forming pressure. The balloons had a double wall thickness of 0.00140 inch. The soft layers were about 1μ thick and the hard layers were about 4μ thick. The balloons burst at about 286 psi and had a calculated burst strength about 26,000 psi.

Example 3

A thirteen layer tubing was formed by coextruding Pebax 7033 and Pebax 5533 in an alternate layer structure. A soft layer of Pebax 5533 was the outermost layer. The material (by thickness) ratio of Pebax 7033 to Pebax 5533 was about 4 to 1. Five 3.0 mm balloons were made from tubing of 0.0184 ID×0.0348 OD (inch). The balloons were formed at 95° C. and 400 psi forming pressure. The balloons had a double wall thickness of 0.00140 inch. The soft polymer layers were about 0.5μ thick. The hard polymer layers were about 2.3μ thick. The balloon bursts at about 288 psi and calculated burst strength was about 26,000 psi.

Example 4

A seven layer tubing was formed by coextruding Pebax 7233 and Pebax 6333 to form an alternate layer structure. The material ratio (by thickness) of Pebax 7233 to Pebax 6633 was about 4 to 1. A soft layer of Pebax 6333 was the outermost layer. Four 3.0 mm balloons were made from tubing of 0.0200 ID×0.0370 OD (inch). The balloons were made at 95° C. and at 360 psi forming pressure. The balloons had a double wall thickness of 0.0015 inch. The soft polymer layers were about 1.2μ thick and the hard polymer layers were 4.8μ thick. The balloons burst at 250 psi.

Example 5

A two layer tubing of 0.020 ID×0.0370 OD was coextruded with the same materials and same material ratio as in Example 2. The outermost layer material was Pebax 5533. Two 3.0 mm balloons were formed at 95° C. and at 450 psi forming pressure. The balloons had a double wall thickness of 0.00175 inch. The soft polymer layer was about 4.4μ thick. The hard polymer layer was about 17.8μ thick. The balloons burst around 323 psi. The calculated burst strength was about 22,000 psi.

In Table 1, the burst performance of this balloon is compared to the performance of the balloon in Example 2.

TABLE 1

| Sample | | 2x Wall | Burst Pressure | Burst Strength (psi) |
| --- | --- | --- | --- | --- |
| Example 3 | 13-Layer (3.0 mm) | 0.00140 | 288 psi | 26,000 |
| Example 5 | 2-Layer (3.0 mm) | 0.00175 | 323 psi | 22,000 |

As the results demonstrate, the balloon in Example 2, with many, thin layers, exhibits higher burst strength than the balloon in Example 4, which has fewer, thicker layers.

Example 6

A balloon puncture test was conducted as follows. Balloons were inflated to 12 atmospheres in a puncture test holder provided with a small hole approximately midway along the balloon body. A pin (2.5 mm×0.45 mm) with a 60° conical point was attached to an MTS tensile tester (Model Sintech 1/G, available from MTS, Carey, N.C. The pin was directed through the hole to engage the balloon and then driven into the balloon at a rate of 0.05 mm/sec until balloon burst. With the same balloon wall thickness (about 0.00140 inch double wall) the two layer balloon size was 3.5 mm and thirteen layer balloon size was 3.0 mm. The 3.5 mm balloons were made as described in Example 5 except the size of balloon mold was larger in order to get the same balloon wall thickness.

The table below illustrates the results for a balloon according to Example 3 and a two layer balloon formed according to Example 5.

TABLE 2

| Sample | | 2x Wall | Puncture Force (g) |
| --- | --- | --- | --- |
| Example 3 | 13-Layer (3.0 mm) | 0.00140 | 108 |
| Example 5 | 2-Layer (3.5 mm) | 0.00140 | 82 |

The puncture force was 108 grams for the thirteen layer balloon and 82 grams for the two layer balloon.

Example 7

A seven-layer tubing was formed by co-extruding Celenex 1700A PBT and Arnitel EM 630 PBT/polyether copolymer in an alternate layer structure. A soft layer of Arnitel EM 630 was the outermost layer. The material (by thickness) ratio of Celenex 1700A to Arnitel EM 630 was about 1.3 to 1. Four 3.0 mm balloons were made from tubing of 0.0190 ID×0.0340 OD (inch). The balloons were formed at 95° C. and 300 psi forming pressure. The balloons had a double wall thickness of 0.00155 inch. The balloon burst at about 330 psi and calculated burst strength was about 25,100 psi. The average thickness of each Celenex layer was 3.7 microns, and the average thickness of each Arnitel/polyether copolymer layer was 2.1 microns.

Example 8

A thirteen-layer tubing was formed by coextruding Vestamid L1801 polyamide 12 and Pebax 7033 poly(amide 12/ether) copolymer in an alternate layer structure. A soft layer of Pebax 7033 was the outermost layer. The material (by thickness) ratio of Vestamid L1801 to Pebax 7033 was about 2.3 to 1. Four 3.0 mm balloons were made from tubing of 0.0200 ID×0.0340 OD (inch). Balloons were formed at 95° C. and 410 psi forming pressure. The balloons had average double wall thickness of 0.00114 inch. The average balloon burst pressure was at 309 psi and the calculated burst strength was at about 33,400 psi. The average thickness of each Vestamid layer was 1.9 microns, and the average thickness of each Pebax layer was 0.7 micron.

Example 9

A thirteen-layer balloon tubing was extruded with Pebax 7233 and a mixture of Pebax 7233 (85% by weight) and Vectra LKX 1111 (15% by weight) in an alternate layer structure. The pure Pebax 7233 was the outermost layer. The material (by thickness) ratio of Pebax 7233 to the mixture was about 9 to 1. Four 3.00 mm balloons were made from tubing of 0.0190 ID×0.0340 OD (inch). The balloons were formed at 95° C. and 410 psi forming pressure. The balloons had an average double wall thickness of 0.00160 inch. The balloons burst at about 390 psi and calculated average burst strength was about 29,100 psi. The average thickness of each Pebax layer was 2.6 microns, and the average thickness of each Pebax/Vectra layer was 0.3 micron.

Example 10

A single layer balloon tubing was extruded with a mixture of Pebax 7233 (99% by weight) and Vectra LKX 1111 (1% by weight). The tubing dimension was ID 0.019×OD 0.036 (inch). One 3.0 mm balloon was formed from the tubing at 95° C. and 480 psi. The balloon had a double wall thickness of 0.00155 inch and burst at 346 psi.

Example 11

A thirteen-layer balloon tubing was extruded with Pebax 7233 and a mixture of Pebax 7233 (90% by weight) and Vectra LKX 1111 (10% by weight) in an alternate layer structure. A soft layer of pure Pebax 7233 was the outermost layer. The material (by thickness) ratio of Pebax 7233 to the mixture in the tubing was about 9 to 1, making the overall material ratio between the Pebax 7233 and the Vectra LKX 1111 approximately 99% to 1%. The balloons burst at about 375 psi with the average double wall thickness of 0.00175 inch. The average thickness of each Pebax layer was 2.9 microns, and the average thickness of each Pebax/Vectra layer was 0.4 micron.

Table 3 compares the burst performance of the balloon of Example 11 to the burst performance of the balloon of Example 10.

TABLE 3

| Sample | | LCP Content | Puncture force at burst (g) |
| --- | --- | --- | --- |
| Example 10 | Single Layer | 1 weight % | 59 |
| Example 11 | Thirteen-Layer | 1 weight % | 104 |

Example 12

A seven-layer balloon tubing was extruded with Pebax 7233 and a mixture of Pebax 7233 (50% by weight) and Vectra LKX 1111 (50% by weight) in an alternate layer structure. A soft layer of pure Pebax 7233 was the outermost layer. The material (by thickness) ratio of Pebax 7233 to the mixture was about 97 to 3 as the individual layer thickness of the mixture was about 2 microns. Two 3.0 mm balloons were made from tubing of ID 0.019×OD 0.036 (inch) at 95° C. and 410 psi forming pressure. The balloons had average double wall thickness of 0.00173 inch. The balloons burst at about 379 psi. The distention from 6 atm to 18 atm was 7.4% as compared to 8.6 percent for a pure Pebax 7233 (single layer without the mixture) balloon. The average thickness of each Pebax layer was 5.3 microns, and the average thickness of each Pebax/Vectra layer was 0.2 micron.

Example 13

A twenty-layer balloon tubing of 0.024 ID×0.065 OD (inch) was extruded with 80% of a mixture of PET Cleartuf 8006 (95% by weight) and Selar (5% by weight) and 20% of a mixture of Hytrel 5556 (80% by weight) and Hytrel 7246 (20% by weight) in an alternate layer structure. Four 5.0 mm balloons were made fiom tubing of ID 0.024×OD 0.065 (inch) at 95° C. and 410 psi forming pressure. The double wall thicknesses of each balloon was 0.0022 inch. The average thickness of each PET Cleartuf/Selar layer was 2.2 microns, and the average thickness of each Hytrel 5556/Hytrel 7246 layer was 0.6 micron.

Example 14

A two-layer balloon tubing was made with the same combination of materials as described in Example 13. A 5.0 mm balloon was made from tubing of ID 0.027×OD 0.063 (inch) at 95° C. and 410 psi forming pressure. The double wall thickness of the balloon was 0.0022 inch.

Table 4 compares testing results from the balloons of Examples 13 and 14.

TABLE 4

| Sample | Burst Pressure (psi) | Compliance | Puncture Force at Burst (g) | Puncture Pin Displacement |
| --- | --- | --- | --- | --- |
| Example 13 | 398 | 3.49% | 1861 | 0.090 inch |
| Example 14 | 363 | 4.70% | 1589 | 0.085 inch |

While certain embodiments have been described, other embodiments are also contemplated. For example, an extrusion apparatus (e.g., a crosshead) having different dimensions can be used. As another example, various channel designs can be used in one or more of the discs, such as a spiral shaped channel that connects the inlet and outlet of a given disc. As an additional example, an extrusion apparatus can have more than one inlet for the polymer composition(s) (e.g., two inlets, three inlets, four inlets, five inlets, six inlets, seven inlets, eight inlets, nine inlets, 10 inlets, 11 inlets, 12 inlets, 13, inlets, 20 inlets, etc.). For example, as shown in FIG. 4, an apparatus can have five inlets (labeled A through E). In certain embodiments, an extrusion apparatus can include one inlet per disc.

Still further embodiments are in the following claims.

The invention claimed is:
1. A multilayer medical balloon produced by radial expansion of a coextrusion, the coextrusion and the balloon comprising four sequential layers, said four sequential layers being arranged in alternating order of:

a first layer of first polymer material which is a first polyamide block copolymer or a first polyester block copolymer, a second layer of a second polymer material of a second polymer material that is harder than said first polymer material, a third layer of said first polymer material, and a fourth layer said second polymer material, the first polymer layers having a layer thickness in the range of from about 0.05 micron to about 5 microns and the second polymer layers having a layer thickness of from about 0.1 micron to about 10 microns.

2. The multilayer medical balloon of claim 1 wherein the balloon includes at least five alternating layers of first polymer material and second polymer material.

3. The multilayer medical balloon of claim 1 wherein the balloon includes at least seven alternating layers of first polymer material and second polymer material.

4. The multilayer medical balloon of claim 3 wherein the balloon includes at least 13 layers alternating layers of first polymer material and second polymer material.

5. The multilayer medical balloon of claim 1 wherein the double wall thickness of the balloon is about 0.0008 inch to about 0.004 inch.

6. The multilayer medical balloon of claim 1 wherein the second polymer material comprises a polymer is selected from the group consisting of thermoplastic polyamides, and thermoplastic polyesters and thermoplastic elastomers.

7. The multilayer medical balloon of claim 6 wherein the second polymer further comprises a liquid crystal polymer.

8. The multilayer medical balloon of claim 1 wherein said first polymer material is said first polyester block copolymer and the second polymer material comprises a polyester.

9. The multilayer medical balloon of claim 1 wherein said first polymer material is said first polyester block copolymer and the second polymer material comprises a second polyester block copolymer.

10. The multilayer medical balloon of claim 1 wherein said first polymer material is said first polyamide block copolymer and the second polymer material comprises a polyamide.

11. The multilayer medical balloon of claim 1 wherein said first polymer material is said first polyamide block copolymer and the second polymer material comprises a second polyamide block copolymer.

12. The multilayer medical balloon of claim 1 wherein the balloon has an inflated diameter of about 1.5 mm to about 6.0 mm.

13. The multilayer medical balloon of claim 12 wherein the balloon has a double wall thickness of from about 0.001 inch to about 0.0022 inch.

* * * * *